(12) United States Patent
Feldmar et al.

(10) Patent No.: US 11,382,615 B2
(45) Date of Patent: Jul. 12, 2022

(54) AUTOMATIC SUTURE DEVICE TO REDUCE BLEEDING IN GASTRIC BYPASS SURGERY

(71) Applicants: Blake Ariel Feldmar, Encino, CA (US); Manooshree Patel, Bakersfield, CA (US); Mariana Guadalupe Alvarez Sandoval, Long Beach, CA (US); Brandon M. Zhang, Goleta, CA (US); Sofia Santos Haile, Palm Desert, CA (US)

(72) Inventors: Blake Ariel Feldmar, Encino, CA (US); Manooshree Patel, Bakersfield, CA (US); Mariana Guadalupe Alvarez Sandoval, Long Beach, CA (US); Brandon M. Zhang, Goleta, CA (US); Sofia Santos Haile, Palm Desert, CA (US)

( * ) Notice: Subject to any disclaimer, the term of this patent is extended or adjusted under 35 U.S.C. 154(b) by 0 days.

(21) Appl. No.: 16/901,426

(22) Filed: Jun. 15, 2020

(65) Prior Publication Data
US 2020/0337692 A1 Oct. 29, 2020

(51) Int. Cl.
*A61B 17/04* (2006.01)
*A61B 17/32* (2006.01)

(52) U.S. Cl.
CPC .. *A61B 17/0469* (2013.01); *A61B 17/320092* (2013.01); *A61B 2017/320082* (2017.08); *A61B 2017/320095* (2017.08)

(58) Field of Classification Search
CPC ........ A61B 17/0469; A61B 17/320092; A61B 2017/0472; A61B 2017/320093
See application file for complete search history.

(56) References Cited

U.S. PATENT DOCUMENTS

| 5,865,361 | A  | * | 2/1999  | Milliman | A61B 17/072 227/176.1 |
| 6,533,795 | B1 | * | 3/2003  | Tran     | A61B 17/0469 606/144  |
| 7,828,798 | B2 |   | 11/2010 | Buysse et al. | |
| 8,303,585 | B2 |   | 11/2012 | Mollenauer | |
| 2005/0021026 | A1 | | 1/2005 | Baily | |

(Continued)

OTHER PUBLICATIONS

Silecchia, G., et al., "Complications of staple line and anastomoses following laparoscopic bariatric surgery", Annals of Gastroenterology, 2018, pp. 56-64, vol. 31.

(Continued)

*Primary Examiner* — Tuan V Nguyen
(74) *Attorney, Agent, or Firm* — Gates & Cooper LLP

(57) ABSTRACT

A disposable reloadable laparoscopic suturing instrument and method for suturing is provided. The disposable reloadable laparoscopic suturing instrument connects to and receives control signals via an actuating instrument. The instrument includes a pair of first and second opposable jaw members, a blade unit, and a needle unit. The jaw members close, clamp onto and secure the tissue, and include a pair of needle tracks and a blade track between the needle tracks. The blade unit has a blade that, upon actuation, travels along the blade track cutting the tissue resulting in an incision. Each needle unit has a needle and thread that, upon actuation, travels along a needle track suturing and sealing the tissue on both sides of the incision.

20 Claims, 17 Drawing Sheets

(56) References Cited

U.S. PATENT DOCUMENTS

| | | | | |
|---|---|---|---|---|
| 2013/0053839 A1* | 2/2013 | Hotto | ................ | A61B 18/1442 |
| | | | | 606/30 |
| 2016/0058437 A1* | 3/2016 | Penna | ................ | A61B 17/0482 |
| | | | | 606/145 |
| 2016/0228145 A1 | 8/2016 | Gleiman et al. | | |
| 2016/0345962 A1* | 12/2016 | Marczyk | ................ | A61B 17/06 |

OTHER PUBLICATIONS

Gundogan, E., et al., "Randomized controlled trial of monopolar cautery versus clips for staple line bleeding control in Roux-en-Y gastric bypass", International Journal of Surgery, 2018, pp. 52-56, vol. 58.

Gastric Bypass Surgery, Center for Metabolic and Weight Loss Surgery, Columbia University Department of Surgery, © 1999-2020, pp. 1-4, as downloaded Oct. 22, 2020, https://columbiasurgery.org/conditions-and-treatments/gastric-bypass-surgery.

Sanchez-Margallo, F.M., et al., "Handheld Devices for Laparoscopic Surgery", IntechOpen, 2018, pp. 75-93, Ch 6.

Jacobsen, H.J., et al., "Management of suspected anastomotic leak after bariatric laparoscopic Roux-en-Y gastric bypass", British Journal of Surgery, 2014, pp. 417-423, vol. 101.

"MicroCutter XCHANGE 30 Stapler: 5mm articulating minimally-invasive stapler", SAGES Webmaster, as downloaded Oct. 22, 2020, https://www.sages.org/publications/tavac/microcutter-xchange-30-stapler-5mm-articulating-minimally-invasive-stapler/, pp. 1-6, © 2020.

Bryans, T., et al., "Poster Highlights Sterility Assurance Levels", Biomedical Instrumentation&Technology, May/Jun. 2010, pp. 240-241, vol. 44, No. 3.

"Endo GIA™ Universal Staplers Product Support", Medtronic, as downloaded Oct. 22, 2020, https://www.medtronic.com/covidien/en-us/support/products/surgical-stapling/endo-gia-universal-staplers-and-reloads.html, pp. 1-6 © 2020.

Kvietys, PR. The Gastrointestinal Circulation. San Rafael (CA): Morgan & Claypool Life Sciences; 2010. Chapter 2, Anatomy, as downloaded Oct. 22, 2020, https://www.ncbi.nlm.nih.gov/books/NBK53099/, pp. 1-5.

"Circulatory System: The Histology Guide", as downloaded Oct. 22, 2020, https://www.histology.leeds.ac.uk/circulatory/arteries.php. Histology Guide © Faculty of Biological Sciences, University of Leeds, pp. 1-3.

"Blood Flow, Blood Pressure, and Resistance", Anatomy and Physiology, OpenStax, 2013 as downloaded Oct. 22, 2020, https://opentextbc.ca/anatomyandphysiology/chapter/20-2-blood-flow-blood-pressure-and-resistance/, pp. 1-24.

Woodford, C., "Sewing machines", Explain that Stuff, Last updated: Apr. 18, 2020, as downloaded Oct. 22, 2020, https://www.explainthatstuff.com/sewingmachines.html, pp. 1-7.

\* cited by examiner

AUTOMATIC SUTURE DEVICE TO REDUCE BLEEDING IN GASTRIC BYPASS SURGERY

BACKGROUND OF THE INVENTION

1. Field of the Invention

The present invention relates generally to surgical suturing devices, and in particular, to a method, apparatus, and article of manufacture for an integrated suturing device that reduces bleeding.

2. Description of the Related Art (Note: This application references a number of different publications as indicated throughout the specification by reference names enclosed in brackets, e.g., [Smith]. A list of these different publications ordered according to these reference names can be found below in the section entitled "References." Each of these publications is incorporated by reference herein.)

Gastric bypass surgery is a procedure to reduce the stomach size of obese patients. To perform the procedure, bariatric surgeons divide the stomach into two parts—a small pouch at the top of the stomach and a large remnant pouch. The small pouch is then connected to the small intestine and serves as a new, smaller stomach leading to decreased appetite and food intake. In the prior art, surgeons perform this division using a surgical stapling device which simultaneously cuts through and seals tissue. FIG. 1 illustrates a prior art surgical stapling device. The stapling device 100 consists of a disposable reloading unit 102 that is connected to an actuating unit 104. The actuating unit includes a handle/trigger 106 mechanism that actuates the disposable reloading unit 102. The stapling device 100 is inserted into patient with the disposable reloading unit 102 in an open position placed over the area of the stomach to be separated. The handle/trigger 106 is depressed causing the disposable reloading unit to transition from an open position to a closed position clamping onto the tissue. Thereafter, an additional mechanism on the actuating unit 104 is used to begin the cutting/stapling process. As a blade of the device reloading unit 102 cuts through tissue 108, the actuating unit 106 causes the reloading unit 102 to seal the tissue 108 on either side of the incision with lines of staples 110. In a typical procedure, 4-5 device reloading units 102 are required to cut through/seal the entire stomach. To reload the device, the device 100 is opened and removed from the body. The surgeon removes the used unit 102 and attaches a new unit 102 to the actuating unit 104. The device is then inserted back into the body, moved to the end of the incision (i.e., at point 112), closed, and actuated again to seal the tissue with further staple lines.

Prior art devices often cause staple-line bleeding along the bowel incision, as the staples are not able to seal tightly enough to prevent blood from leaking through. The staple-line typically appears clean initially; however, the tissue is "stunned" upon initial cutting and stapling. As the tissue relaxes and blood vessels dilate, bleeding begins along the staple-line and is evident within 10-15 minutes after stapling.

In the prior art, surgeons must use an additional device to further seal the tissue in these cases, typically utilizing a monopolar cautery pen to cauterize any bleeding spots along the staple-line. Many solutions have been proposed to try to solve this problem (e.g. buttressing, thrombin matrix, fibrin glue)([Silecchia]) but none have been satisfactory.

In view of the above, what is needed is a mechanism to minimize bleeding without the need for additional tools. Specifically, the top three needs to overcome the problem are: (1) the solution leads to minimal or no bleeding; (2) the solution lasts permanently inside the bowel tissue; and (3) the solution is able to target the correct tissue.

The first need addresses the main problem, chiefly the need to reduce bleeding both intra- and post-operatively. Some form of intraoperative staple-line bleeding occurs nearly every time the procedure is formed according to one or more gastric surgeons with the International Journal of Surgery reporting 50±59 ml of blood typically lost through the staple line with use of monopolar cauterization ([Gundogan]). In some cases, this bleeding can have severe consequences. Post-operative bleeding can necessitate blood transfusions (around 5% of cases), or if severe enough can require the patient to be opened back up for additional surgical repair (1.4%) ([Silecchia]). Additionally, internal bleeding post-surgery has a 0.5% mortality rate ([Gastric]). Minimizing bleeding is thus crucial to improving surgical outcomes for patients.

The second need is for the solution to last permanently. Staples are made of titanium, an inert, biocompatible material that can remain in the body indefinitely with no ill effects ([Kasemo]). As such, the seal created by the staples lasts permanently. Any alternative solution would need to maintain this longevity. The ability to permanently seal the bowel tissue will prevent patients from enduring additional risk post-surgery and minimize potential complications.

The last need is to target the correct stomach tissue. The device must be precise; the prior art stapler design has four (4) degrees of freedom ([Sanchez-Margallo]), so a device with the same or more rotational freedom is desired. The device must also be laparoscopically compatible in order to target the correct tissue, meaning it must contain the ability to maneuver during laparoscopic surgery and must be appropriately sized to be usable in a single laparoscopic port.

Reducing bleeding was identified as the top need to address. Thus, a solution should minimize bleeding in laparoscopic (roux-en-y) gastric bypass surgeries in order to decrease the need for multiple sealing methods during surgery, follow-up care and/or follow-up surgery, and patient mortality rates.

SUMMARY OF THE INVENTION

Prior art gastric bypass devices simultaneously cut and seal stomach tissue by placing three lines of staples on either side of the incision. However, these staples are often unable to completely seal the tissue, and bleeding occurs along the staple-line. Embodiments of the invention minimize bleeding in laparoscopic (roux-en-y) gastric bypass surgeries in order to decrease the need for multiple sealing methods during surgery, follow-up care and/or follow-up surgery, and patient mortality rates. Embodiments of the invention provide an automatic suturing device that utilizes a two-track approach and forcep compression.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

Figure 1:
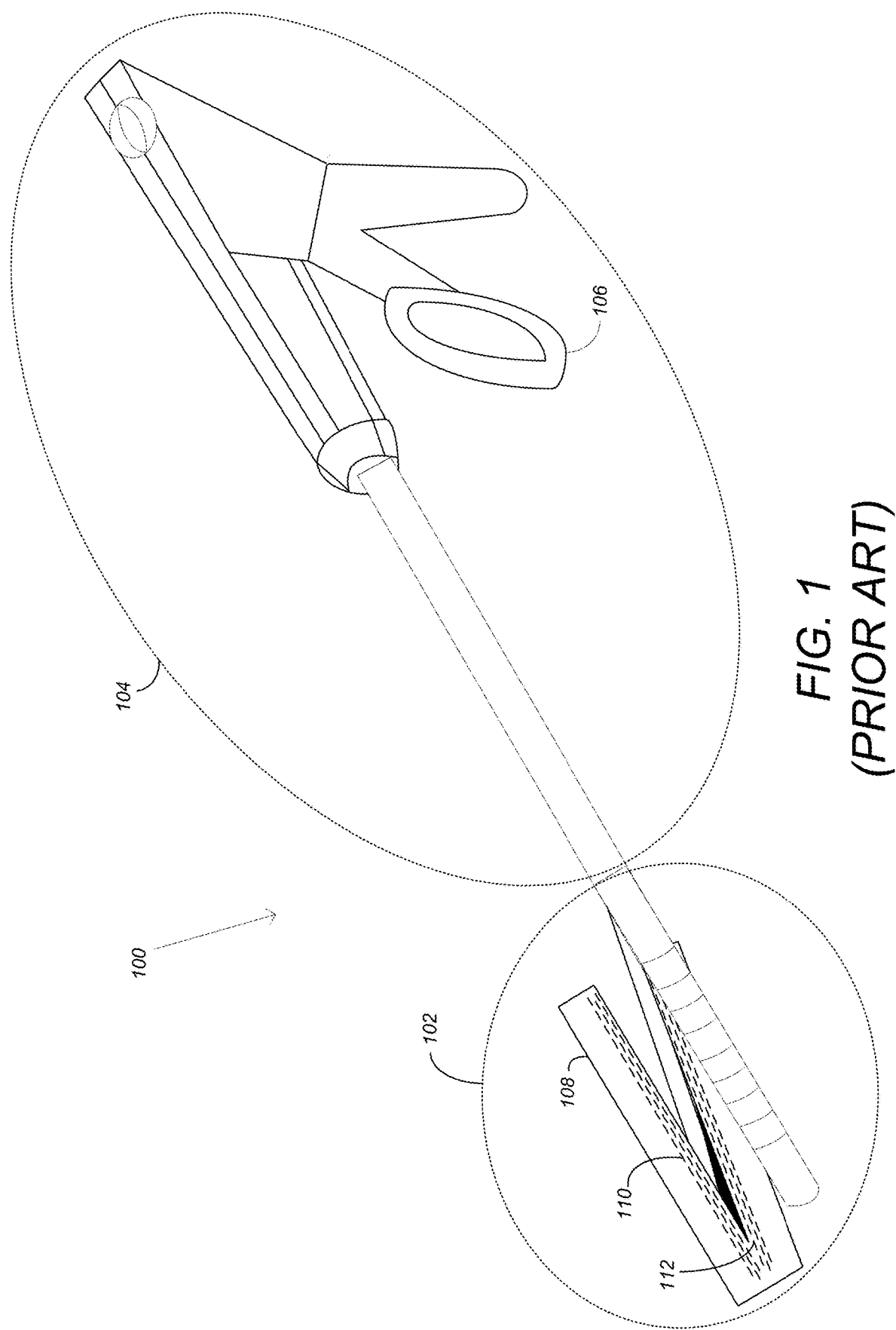
FIG. 1 illustrates a prior art surgical stapling device.
Figure 2A:
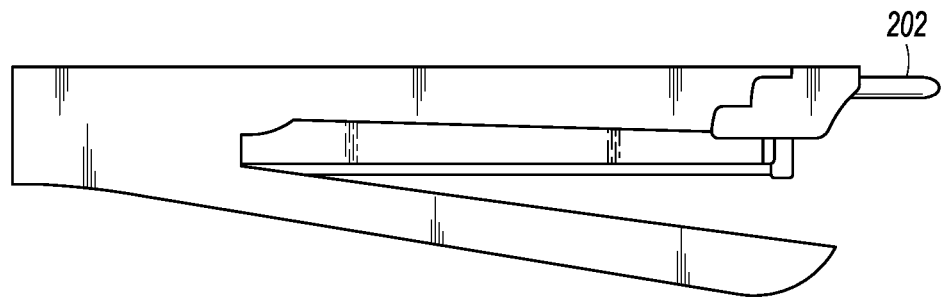
FIG. 2A illustrates a stapler with built-in cauterization functionality in accordance with one or more embodiments of the invention.
Figure 2B:
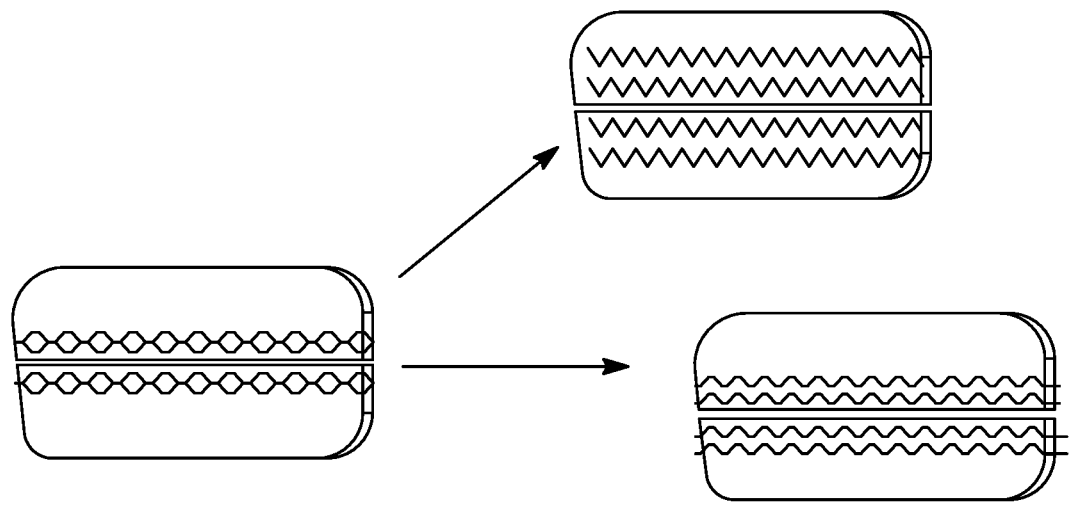
FIG. 2B illustrates a stapler that uses a triangle staple pattern with an extra line of staples in accordance with one or more embodiments of the invention.
Figure 2C:
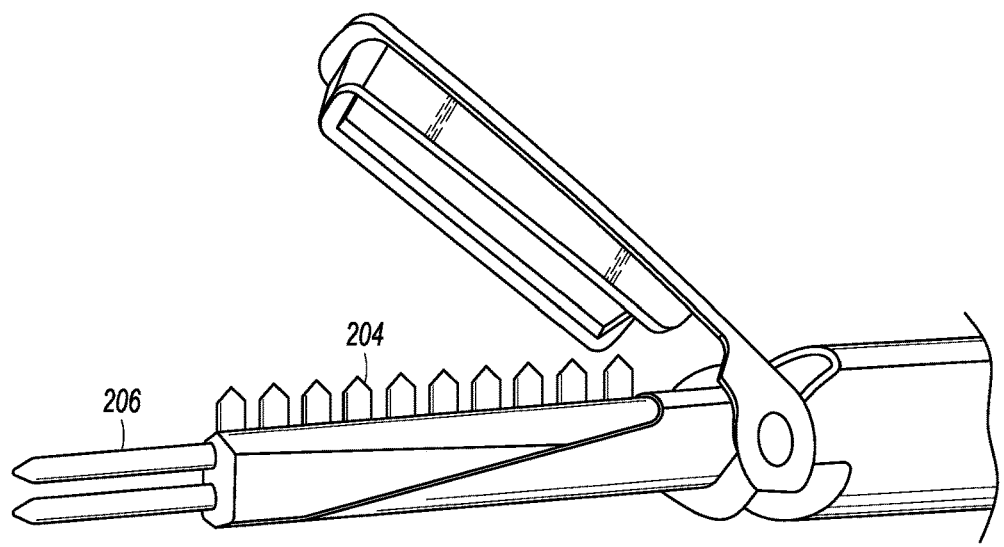
FIG. 2C illustrates an ultrasonic sealing stapler in accordance with one or more embodiments of the invention.
Figure 2D:
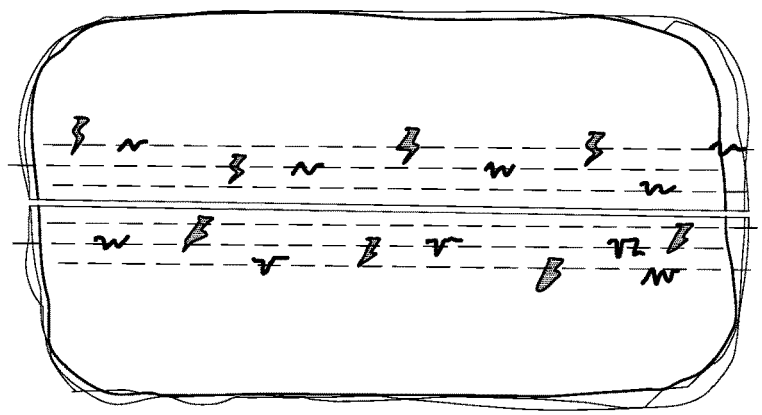
FIG. 2D illustrates a stapler in which the staples themselves cauterize in accordance with one or more embodiments of the invention.
Figure 2E:
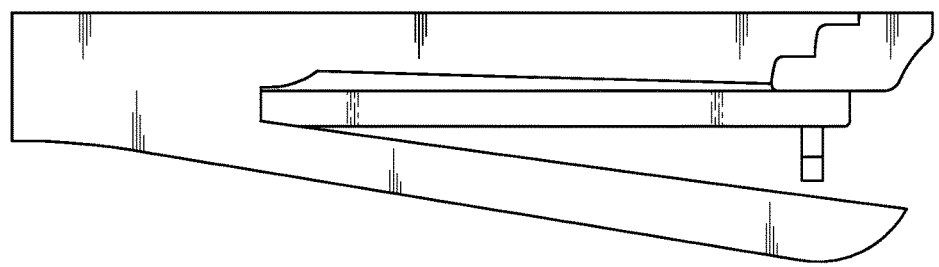
FIG. 2E illustrates an automatic suturer in accordance with one or more embodiments of the invention.

In the following description, reference is made to the accompanying drawings which form a part hereof, and which is shown, by way of illustration, several embodiments of the present invention. It is understood that other embodiments may be utilized and structural changes may be made without departing from the scope of the present invention.

Establishing Target Specifications

Thirteen metrics were defined to address the top three needs. Table 1 illustrates a best-estimate table of metrics for top needs in accordance with one or more embodiments of the invention. The importance of each of these metrics is noted in Table 1, with 1 being the least important and 5 being the most.

TABLE 1

| Metric No. | Need No. | Metric | Units | Importance |
|---|---|---|---|---|
| 1 | 1, 2 | Biocompatibility | FDA Class | 3 |
| 2 | 3 | Device diameter | Millimeters | 3 |
| 3 | 3 | Length of bowel sealed per use | Millimeters | 4 |
| 4 | 1, 2 | Incidence of major post-operative staple-line bleeding | Percentage | 5 |
| 5 | 1 | Volume of intraoperative staple-line bleeding | Milliliters | 5 |
| 6 | 1, 2 | Anastomotic leak rate | Percentage | 5 |
| 7 | 1 | Sealant activation rate | Minutes | 4 |
| 8 | 3 | Number of laparoscopic ports required | Number of ports | 3 |
| 9 | 3 | Length of internal apparatus | Centimeters | 3 |
| 10 | 1 | Sterility Assurance Level | Integer | 3 |
| 11 | 3 | Number of steps to operate device | Number of steps | 1 |
| 12 | 3 | Degrees of freedom | DoF | 3 |
| 13 | 1, 2 | Percent of surgeries that require follow-up care | Percentage | 5 |

Table 2 illustrates a needs-metrics matrix that depicts a visualization of the needs that each metric meets in accordance with one or more embodiments of the invention.

TABLE 2

| | Metrics | | | | | | |
|---|---|---|---|---|---|---|---|
| Need | 1 Bio-compatibility | 2 Device Diameter | 3 Length of bowel sealed per use | 4 Incidence of major post-operative staple-line bleeding | 5 Volume of intraoperative staple-line bleeding | 6 Anastomotic leak rate | 7 Sealant activation rate |
| 1 The solution leads to little or no bleeding | • | | | • | • | • | • |
| 2 The solutions lasts permanently | • | | | • | | • | |

TABLE 2-continued

| Need | Metrics | | | | | |
|---|---|---|---|---|---|---|
| | 8 Number of laparoscopic ports required | 9 Length of internal apparatus | 10 Sterility Assurance Level | 11 Number of steps to operate device | 12 Degree of freedom of device | 13 Percent of surgeries that require follow-up care |
| 3 The solution targets the correct stomach tissue | | | • | | | • |
| 1 The solution leads to little or no bleeding | | | | | | • |
| 2 The solutions lasts permanently | | | | | | • |
| 3 The solution targets the correct stomach tissue | • | • | | • | • | |

The top identified need, which was minimizing bleeding, has seven corresponding metrics: biocompatibility, incidence of major postoperative staple-line bleeding, volume of intraoperative staple line bleeding, anastomotic leak rate, sealant activation rate, sterility assurance level, and percent of surgeries that require follow up care.

Biocompatibility is crucial for any material being placed inside the body, as incompatible materials can result in immune reactions from the body such as an inflammatory response ([Nilsson]). As such, using an incompatible material could end up causing more bleeding and ill effects rather than minimizing these problems. Similarly, using devices consisting of and/or with materials that are not completely sterile can cause infection and other harm to the body, potentially exacerbating any existing bleeding. For these reasons, biocompatibility and sterility assurance level are relevant metrics.

Incidence of major postoperative staple-line bleeding is relevant to the top identified need because the percentage of bleeding post-surgery would illustrate whether the solution prevented bleeding or not. Similarly, volume of bleeding and leakage rate would also indicate how well the device is able to seal the tissue. Sealant activation rate is also an important metric to examine, since the faster the sealant can seal the tissue, the more likely it is to mitigate bleeding. Finally, the percentage of surgeries requiring follow up care is a necessary metric because most post-surgical complications are related to internal bleeding ([Jacobsen]).

Based on benchmark values from the Endo GIA stapler as well as from various literature sources, marginal and ideal values for each metric were defined. Table 3 illustrates target specifications in accordance with one or more embodiments of the invention.

TABLE 3

| Metric | Units | Marginal Value | Ideal Value |
|---|---|---|---|
| Biocompatibility[11] | FDA Class | Class II | Class III |
| Device diameter[12] | Millimeters | 5-15 mm | <5 mm |
| Length of bowel sealed per use[13] | Millimeters | 30-60 mm | 60 mm |
| Incidence of major post-operative staple-line bleeding[4] | Percentage | 2% | <2% |
| Volume of intraoperative staple-line bleeding[5] | Milliliters | 25 ml | <10 ml |
| Chance of Anastomotic leakage[10] | Percentage | 0.1-5.6% | <0.1% |
| Sealant activation rate[14] | Minutes | 4-10 min | 0-4 min |
| Number of laparoscopic ports required[6] | Number of ports | 2 | 1 |
| Length of internal apparatus[12] | Centimeters | 26 cm-30 cm | <26 cm |
| Sterility Assurance Level[15] | Integer | $10^{\wedge}-4$ | $10^{\wedge}-6$ |
| Number of steps to operate device[16] | Number of steps | 13-16 | <13 |
| Degrees of freedom[16] | DoF | 4 | 6 |
| Percent of surgeries that require follow-up care[4] | Percentage | <2% | 0 |

Embodiments Overview

Embodiments of the invention may include various different implementations that address the problem of bleeding. One exemplary embodiment consists of modifying the prior stapler devices, and combining it with existing technologies to best optimize the benefits of various sealing methods. Alternative embodiments include alternatives to the stapler entirely. Generally, the different embodiments/concepts may be grouped into five categories: suturing methods, cauterizing methods, buttressing methods, surgical glue-based methods, and methods involving changing the current staple pattern. An additional outlier embodiment/concept, the ultrasonic stapler, did not fall into any of these categories. "Mix-and-match" concepts combining ideas from across these groups were also considered. Various embodiments/concepts are summarized below in Table 4.

TABLE 4

| Category | Concepts |
|---|---|
| Staple Patterns | Triangle shaped staple line<br>X shaped staples<br>4 (or more) lines of staples |

TABLE 4-continued

| Category | Concepts |
|---|---|
| | Staples inserted from both sides of tissue |
| | A consistent line instead of r |
| | multiple little ones created by staple |
| | Interlocking Teeth Closure [Resembling a zipper pattern] |
| | Cauterizing staples |
| | (staples themselves either heated or electrified) |
| Suturing | Automatic Suturer |
| | After cut, sutures with PTFE which is biodegradable |
| | After cut, sutures with PLA (longer lasting than Teflon) |
| Cautery | Hot blade—cauterizes as it cuts |
| | Added/built-in cauterizer—end part of stapler would have a deployable cautery tool → when you're donestapling, you click a button and functionality switches over to cauterizing |
| | Hot/electric staples |
| | Heated scissor blades |
| | Laser cut the tissue, laser should also be hot enough to cauterize |
| | Clamping and ironing the tissue |
| Buttressing | Synthetic buttressing + button-triggered fibrin glue release |
| | Synthetic buttressing + automatic fibrin glue release as you cut |
| | Heated buttressing |
| Surgical Glues | Hot blade coated in fibrin glue |
| | Spray on hydrogel elastic/adhesive surgical glue made of methacryloyl-substituted tropoelastin that seals in under 60 seconds |
| | Ultrasonic stapler |

Based on practical testing/experimentation and literature, embodiments of the invention described herein focus on five of these alternatives. FIGS. 2A-2E illustrates such embodiments. Further, each of the illustrated embodiments may replace the disposable reloading unit 102 of FIG. 1 and be configured to connect to an actuating unit 104. These embodiments are (FIG. 2A) a stapler with built-in cauterization functionality; (FIG. 2B) a stapler that uses a triangle staple pattern with an extra line of staples; (FIG. 2C) an ultrasonic sealing stapler; (FIG. 2D) a stapler in which the staples themselves cauterize (e.g., cauterizing staples made of conductive biocompatible polymers); and (FIG. 2E) an automatic suturer.

The cauterizing stapler (FIG. 2A) features a monopolar cauterizer (similar to a cautery pen) at the tip 202 of the stapler cartridge. This cauterizer is retractable, meaning it can retract in and out of the tip 202 of the stapler at the click of a button. This feature allows the user to quickly and easily switch between stapling and cauterizing functionalities based on what the situation requires.

The triangle staple pattern (FIG. 2B) overcomes the problems of the prior art linear staple pattern that allows blood to easily seep through the staple lines. Similar to pinball machine paddles, the triangle pattern prevents blood from seeping through. Additionally, adding another line of staples adds an extra layer of securely sealing the tissue.

The ultrasonic stapler (FIG. 2C) is based on the harmonic scalpel, which utilizes ultrasonic vibrations rather than electricity to simultaneously cut and cauterize tissue. Rather than a blade, the ultrasonic stapler utilizes a harmonic scalpel to cut the tissue using frictional energy. Such an ultrasonic stapling generates very little if any bleeding, while retaining normal stapling functionality so as to securely seal the tissue. Nonetheless, it may be noted that in FIG. 2C, weak energy may be created by the jaw/teeth 204 and dangerous stray energy may be produced at the distal tip 206. As a result, stray energy may be lost out of the distal tip 206 with weak frictional energy create by the jaw 204.

The stapler with self-cauterizing staples (FIG. 2D) involves running a current through the staples so that the staples themselves will cauterize. Because currently used staples are made of nonconductive materials (typically titanium), such embodiments of the invention include new staples from conductive biocompatible polymers. Conductive biocompatible polymers are described in [He]. Embodiments of the invention shape such polymers into staples, insert the staples in the stapler, and electrify the staples such that the staples cauterize as they are driven/applied/used by the stapler during surgery.

The automatic suturer (FIG. 2E) replaces the stapler entirely with an equivalent device that utilizes sutures rather than staples for sealing. Similar to the stapler, the suturer would have a blade in the middle, then would automatically suture both sides of the tissue as it cuts.

Embodiment Evaluation

Table 5 illustrates an evaluation/selection matrix used to evaluate the above-identified five embodiments.

TABLE 5

| Criteria | Weight | Reference-Covidien Endo GIA Stapler | | Built-In Cauterization | | Triangle Staple Pattern | |
|---|---|---|---|---|---|---|---|
| Takes minimal time | 0.15 | 3 | 0.45 | 4 | 0.6 | 4 | 0.6 |
| Targets correct tissue | 0.15 | 3 | 0.45 | 3 | 0.45 | 3 | 0.45 |
| Seals tissue | | | | | | | |
| Leads to minimal bleeding | 0.2 | 3 | 0.6 | 5 | 1 | 4 | 0.8 |
| seal lasts permanently | 0.25 | 3 | 0.75 | 4 | 1 | 4 | 1 |
| Maneuverability | 0.1 | 3 | 0.3 | 3 | 0.3 | 3 | 0.3 |
| Novelty | 0.15 | 3 | 0.45 | 1 | 0.15 | 4 | 0.6 |
| Total | 1 | | 3 | | 3.5 | | 3.75 |

| Criteria | Weight | Ultrasonic Stapler | | Cauterizing Staples made of Conductive Biocompatible Polymers | | Automatic Suturer | |
|---|---|---|---|---|---|---|---|
| Takes minimal time | 0.15 | 5 | 0.75 | 4 | 0.6 | 4 | 0.6 |
| Targets correct tissue | 0.15 | 3 | 0.45 | 3 | 0.45 | 3 | 0.45 |
| Seals tissue | | | | | | | |
| Leads to minimal bleeding | 0.2 | 5 | 1 | 4 | 0.8 | 5 | 1 |
| seal lasts permanently | 0.25 | 5 | 1.25 | 4 | 1 | 5 | 1.25 |
| Maneuverability | 0.1 | 3 | 0.3 | 3 | 0.3 | 2 | 0.2 |
| Novelty | 0.15 | 2 | 0.3 | 5 | 0.75 | 5 | 0.75 |
| Total | 1 | | 4.05 | | 3.9 | | 4.25 |

Table 5 utilizes five primary criteria to systematically compare the above-identified five embodiments, with the current device (COVIDIEN™ Endo GIA stapler) used as a benchmark. The first criteria was that the solution should take minimal time to use, as increased surgical times are one of the main problems with the prior art devices. The second criteria was that the solution targets the correct tissue, meaning that it can accurately cut and seal the desired portion of the stomach or bowel. The third criteria, seals tissue, was split into two sub-criteria. The first sub-criteria was that the solution should lead to minimal bleeding, as bleeding is the one of the problems that the present invention solves. The second sub-criteria was that the seal should last permanently, as impermanence would result in increased follow-up care and potentially additional surgery. The fourth criteria was maneuverability, meaning that the solution should be easily adjustable/rotatable laparoscopically within the abdominal cavity. Finally, the fifth criteria was the novelty of the solution based on an evaluation of current literature including patents.

Built-in cautery takes the current standard of care (cutting/stapling and then spot cauterizing) and reduces the number of devices required from two to one. Due to the compliance with the standard of care, such a device successfully seals the tissue.

Conversely, as little to no literature exists comparing the efficacies of different staple patterns, embodiments of the invention provide a novel triangle staple pattern.

Alternative embodiments include the ultrasonic stapler as it enables cutting and sealing tissue with little to no bleeding.

Alternative embodiments may also include cauterizing staples in which the staples themselves cauterize to prevent bleeding from occurring. Such cauterizing staples may consist of a conductive biocompatible polymer such as that described in [He]. In contrast, prior art staples are made of nonconductive materials.

Additional embodiments may include the automatic suturer that addresses many of the problems posed by the other embodiments. The suturer is novel, as the prior art fails to describe a device that cuts and also sutures on each side of that cut. Suturing is an accepted and highly effective sealing method; unlike staples, there are no gaps in a suture line and so bleeding is typically minimal. Some bariatric surgeons even suture over the staple lines generated by the current device in gastric bypass surgery as an additional sealing method (see [Silecchia]). However, the automatic suturer is not without faults. Automated suturing is more mechanically and electrically complex than stapling, and as such bulkiness, precision, and maneuverability are potential concerns.

Details for Automatic Suturer

As described above, embodiments of the invention include an automatic suturer with a cauterizing needle. The automatic suture device overcomes the problems of the prior art and further enables proper sealing. Tight, permanent sealing of tissue minimizes the time required for surgery as it reduces the need for additional sealing methods and tools. Thus, the automatic suturer both saves surgeons time and effort and improves patient outcomes. The device design preserves the ability to target the correct tissue. Although maneuverability may slightly suffer (compared to the prior art laparoscopic staplers) due to the bulkiness of the suturing mechanism, this concern was far overshadowed by the device's superiority in other areas.

Figure 3:
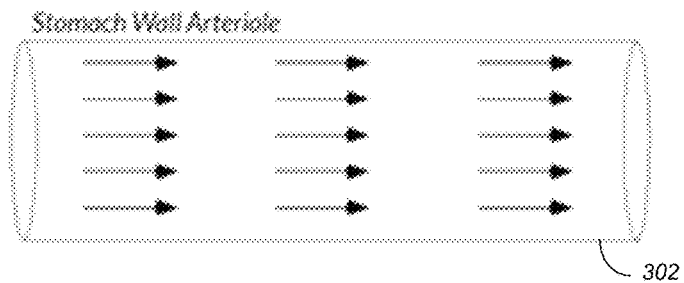
FIG. 3 illustrates blood flow through submucosal arteriole in accordance with one or more embodiments of the invention.
Figure 4:
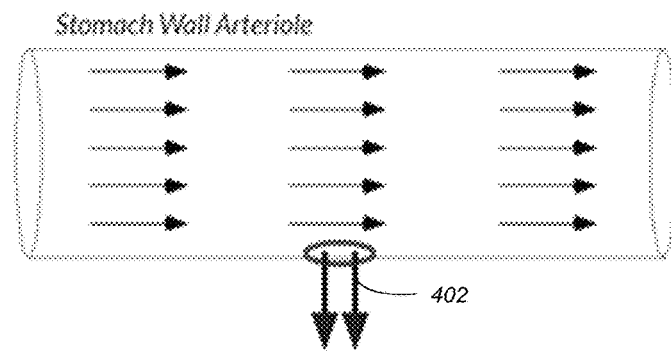
FIG. 4 illustrates arteriole bleeding in accordance with one or more embodiments of the invention.

An analysis of the amount of bleeding generated by the prior art device provides a metric for comparison to embodiments of the invention. The main source of bleeding originates from blood vessels in the stomach wall (i.e. the submucosa of the gastrointestinal tract). Exploration of relevant vascular anatomy reveals that the most predominant blood vessels in the submucosa are arterioles ([Kvietys]). Calculations were thus performed using a mathematical model of blood flow through a submucosal arteriole. FIGS. 3 and 4 illustrate blood flow through submucosal arteriole. As illustrated, the arteriole may be modeled as a nonelastic pipe 302, while laminar and plug flows may be assumed. Relevant arteriole properties are listed in Table 6.

TABLE 6

| Variable | Value |
|---|---|
| Arteriole radius ($R_{arteriole}$) | 0.005 cm[25] |
| Maximum velocity of blood flow through arteriole ($V_{max, arteriole}$) | 6 cm/second[26] |

Flow can be described using Equation 1, where $q_v$ represents the volumetric flow rate, R represents the radius, and $V_{max}$ represents the maximum velocity.

$$q_v = \pi R^2 \frac{V_{max}}{2} \qquad \text{EQ. 1}$$

Applying this equation to blood flow through the submucosal arteriole yields the following:

$$q_v = \pi R_{arteriole}^2 * \frac{V_{max,arteriole}}{2} = \pi(0.005 \text{ cm})^2 * \frac{6 \text{ cm/s}}{2} = 2.36 * 10^{-4} \frac{\text{cm}^3}{\text{s}}$$

Figures 5A, 5B:
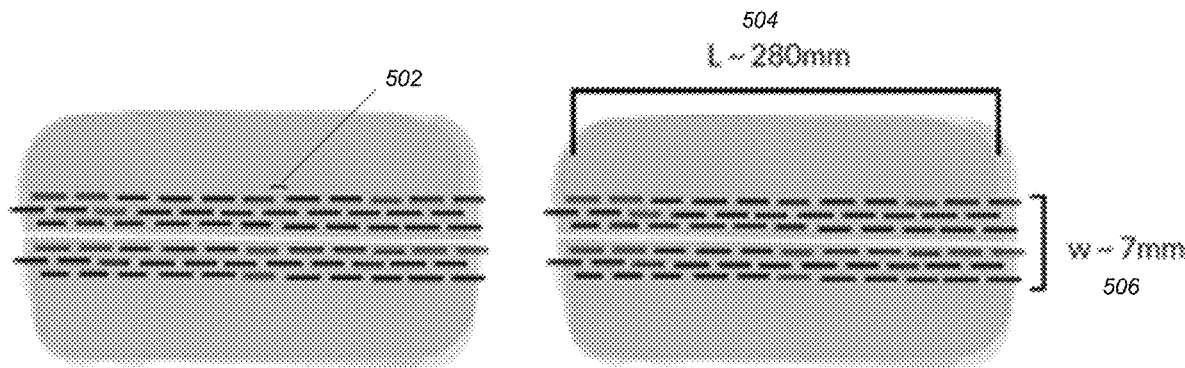
FIG. 5A illustrates the distance between staples in accordance with one or more embodiments of the invention.
FIG. 5B illustrates staple line dimensions in accordance with one or more embodiments of the invention.

After determining the normal volumetric flow rate, this information was used to estimate the flow associated with bleeding (FIG. 4 illustrates arteriole bleeding 402 in accordance with one or more embodiments of the invention). Referring to FIGS. 5A and 5B, bleeding was assumed to be coming from the small gaps 502 between each staple; this distance was measured to be 1 mm (FIG. 5A illustrates the distance 502 between staples in accordance with one or more embodiments of the invention). The radius of each hole through which blood could exit the arteriole is thus 0.5 mm. The flow profile was assumed to remain constant upon exiting the arteriole.

Using this information as well as the normal volumetric flow rate, the velocity of blood exiting the arteriole may be calculated as:

$$V_{max,bleeding} = \frac{2q_v}{\pi R_{hole}^2} = \frac{2\left(2.36 * 10^{-4} \frac{\text{cm}^3}{\text{s}}\right)}{\pi(0.05 \text{ cm})^2} = 0.06 \frac{\text{cm}}{\text{s}}$$

Finally, this velocity was multiplied by the length and width of the staple-line in order to calculate the total volume of blood lost per second through staple-line bleeding. FIG. 5B illustrates staple line dimensions 504 (length of 280 mm) and 506 (width of 7 mm) in accordance with one or more embodiments of the invention.

Volume of blood lost per second =

$$V_{max,bleeding} Lw = \left(0.06 \frac{\text{cm}}{\text{s}}\right)(28 \text{ cm})(0.7 \text{ cm}) = 1.176 \frac{\text{cm}^3}{\text{s}} = 1.18 \frac{\text{mL}}{\text{s}}$$

To contextualize this value, standard measurements of blood loss during surgery may be examined. Maximum allowable blood loss (MABL) is the most accurate metric used to determine the maximum amount of blood a patient can lose before requiring transfusion, and is calculated based on patient age, weight, and hematocrit (Equation 2).

$$MABL = EBV * \frac{HCT_{initial} - HCT_{acceptable}}{HCT_{initial}} \qquad \text{EQ. 2}$$

where EBV is estimated blood volume (function of age/weight), $HCT_{initial}$ is the initial hematocrit, and $HCT_{acceptable}$ is the lowest acceptable hematocrit.

Because MABL is so individualized, it is difficult to use for contextual purposes. More generalized guidelines are provided by the American College of Surgeons, which defines four classes of acute hemorrhage ([Manning]). These classes are based on the MABL for a 70-kg male, and are summarized in table 7:

TABLE 7

Classes of Hemorrhagic Shock Based on Percentage of Blood Loss Blood Loss*

| 0%-15% or up to 750 mL | 15%-30% or 750 mL-1,550 mL | 30%-40% or 1,500-2,000 mL | >40% or >2,000 mL |
| --- | --- | --- | --- |
| Minimal tachycardia | Tachycardia | Tachycardia | Marked Tachycardia |
| Normal or increased pulse pressure | Tachypnea | Tachypnea | Decreased systolic blood pressure |
| | Decrease in pulse pressure | Decreased systolic blood pressure | Narrowed pulse pressure |
| | Cool clammy skin | Oliguria | Markedly decreased (or no) urinary output |
| | Delayed cap refill | Changes in mental status such as confusion or agitation | Loss of consciousness |
| | Slight anxiety | | Cold, pale skin |

*These guidelines are for a 70-kg adult make.

Specific clinical recommendations are associated with each class. Class I blood loss will generally heal on its own, with no intervention usually necessary. Class II blood loss requires replacement of fluid, but generally not blood transfusion. At Class III, however, blood transfusion is necessary and stopping the hemorrhage becomes top priority. Finally, Class IV represents immediate life-threatening circumstances and requires full surgical intervention ([Manning]).

With 1.18 mL of blood being lost through the staple-line every second, 750 mL of blood would be lost after just 10-11 minutes, making the blood loss a class II hemorrhage. Another 10-11 minutes of bleeding would mean 1550 mL of blood lost, and bring the hemorrhage up to a class III categorization. Although this model does assume bleeding is occurring at every single gap between staples (while in reality at least some of the staples typically seal properly), the data clearly shows that at its worst staple-line bleeding can be a real problem, especially if left untreated.

One large advantage of suturing over stapling is that there are no gaps in a suture line, but rather one continuous thread. Elimination of gaps eliminate all bleeding based on this model, as the only sources of bleeding were the holes between staples. However, some bleeding may still occur. The above analysis and benchmark values can thus be used as useful comparisons during testing for understanding how well an automatic suturer performs at minimizing bleeding.

Implementation Details and Testing

The automatic suturer design embodiments were further developed through the use of CAD models as well as multiple prototypes. A first feature of embodiments of the invention is a two-track approach. In most ways, automatic suturer technology is similar to that of a sewing machine. Both utilize an automated electromechanical system to rapidly move a needle up and down, creating a stitch through interactions between the needle, bobbin, and shuttle ([Woodford]). However, in a sewing machine, the material being sewn (e.g., cloth or "tissue") must be moved manually through the machine by the user, with the needle remaining in one stationary position. This mechanism would not work inside the body, as moving tissue precisely through the device laparoscopically (while simultaneously holding the device still) would be extremely difficult for the surgeon. Instead, the needle is programmed to move along a track, bobbing up and down as usual while also moving laterally in order to thread a precisely defined line. Prior art suturers only describe/have one needle track. Additionally, none are combined with a blade. The design of embodiments of the invention utilizes two needles positioned on parallel tracks in order to suture alongside each side of a cut. Of note is that typical sewing machine needles are straight while suturing needles of embodiments of the invention may be curved. As the suturer's blade cuts through tissue, a line of sutures will simultaneously seal the tissue on either side of the incision.

A second feature of embodiments of the invention is its forcep compression. Similar to the compression principle of the staple, embodiments of the invention mimic the compression mechanism in a laparoscopic forcep. The teeth are designed in a way to firmly grasp the tissue without causing it any harm.

Figure 6A:
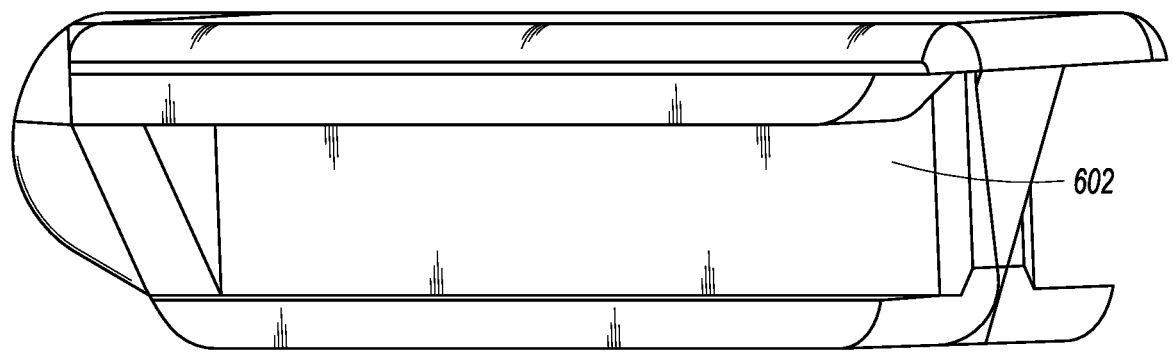
FIGS. 6A and 6B illustrate computer-aided design renderings of the automatic suturer unit in accordance with one or more embodiments of the invention.
Figure 6B:
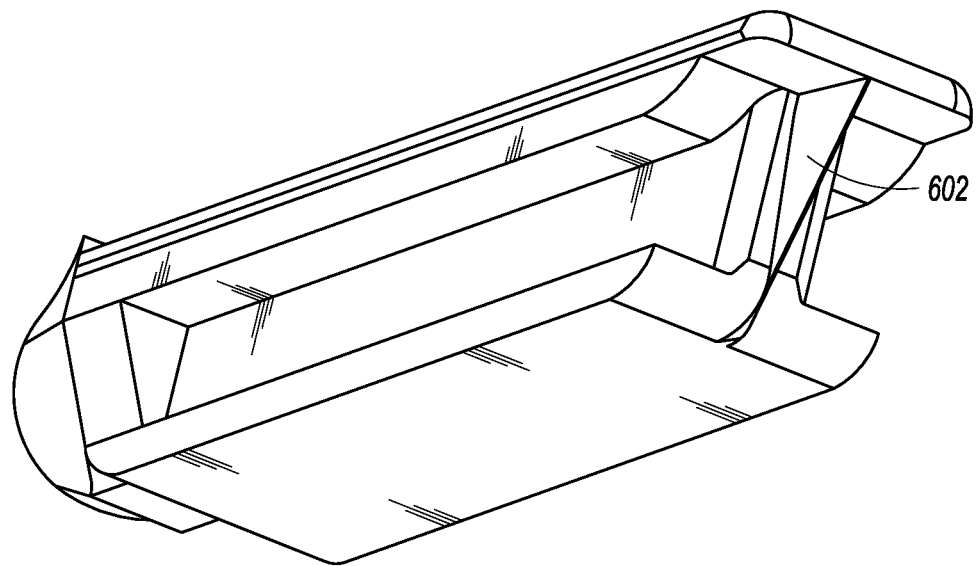
Figure 7B:
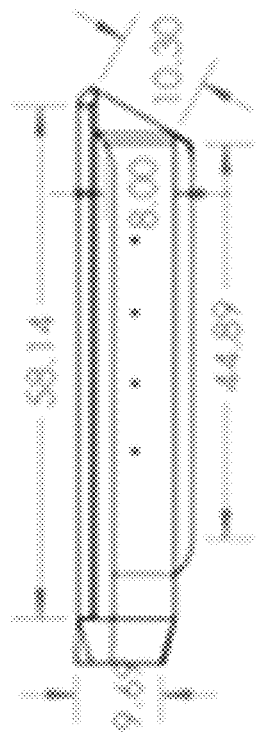
FIGS. 7A-7D illustrate engineering drawings depicting different views of a closed device in accordance with one or more embodiments of the invention.
Figure 7D:
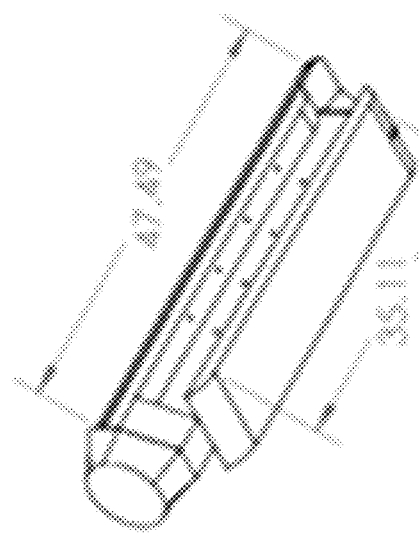
Figure 7A:
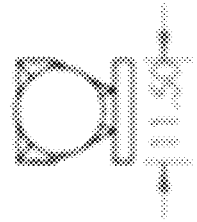
Figure 7C:
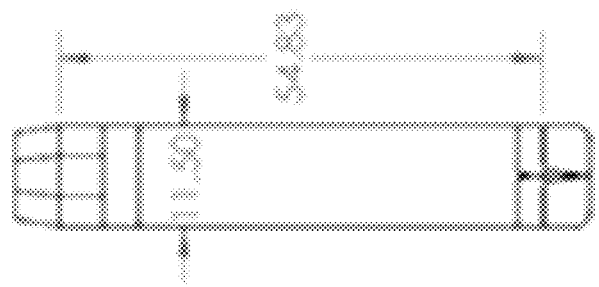
Figure 8A:
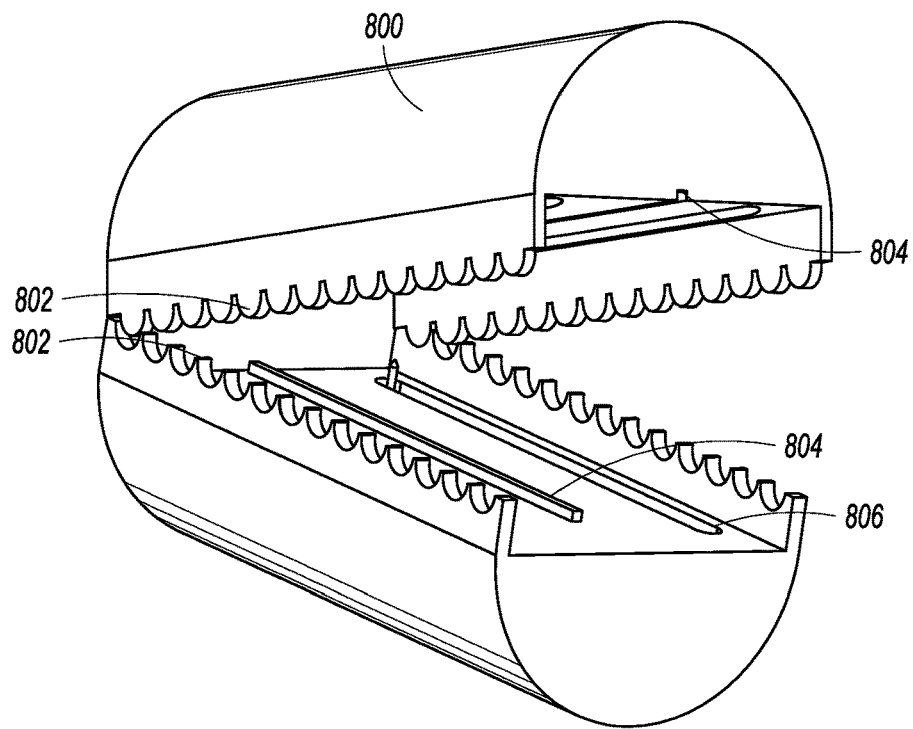
FIGS. 8A-8C illustrate an open device with visible forceps that when closed will clamp onto the stomach issue securing the device and tissue in place in accordance with one or more embodiments of the invention.
Figure 8B:
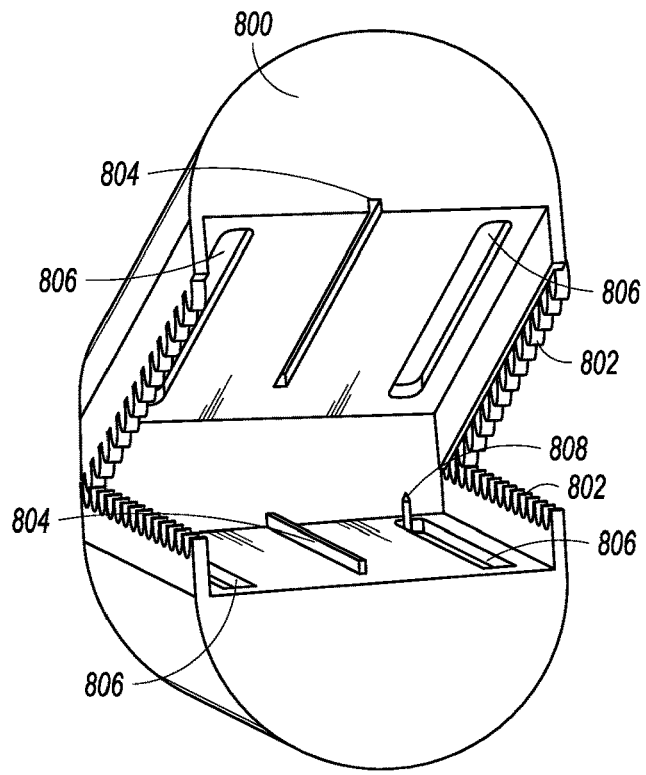
Figure 8C:
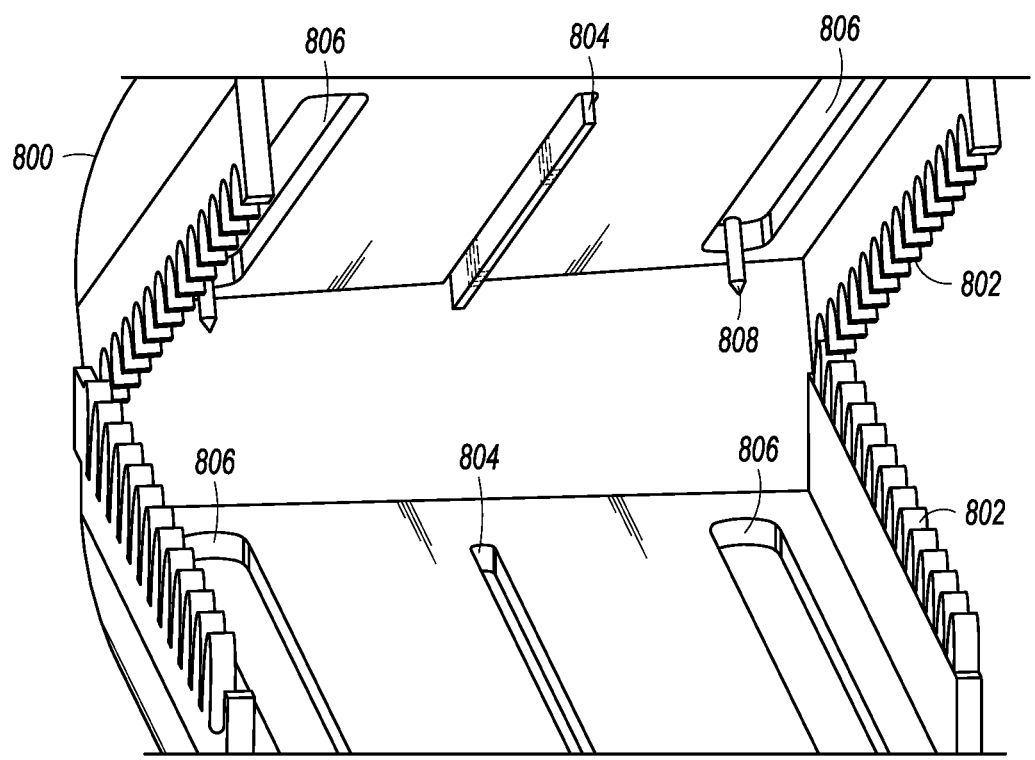

FIGS. 6A and 6B illustrate CAD (computer-aided design) renderings of the automatic suturer unit in accordance with one or more embodiments of the invention. The devices illustrated would be attached to an actuating unit that would trigger the suturing. Specifically, FIGS. 6A and 6B illustrate a closed/clamped device with a visible blade 602. Similarly, FIGS. 7A-7D illustrate engineering drawings (with dimensions listed in millimeters) depicting different views of a closed device in accordance with one or more embodiments of the invention. FIG. 7A illustrates a rear view of the removable suture head, showing the side that would be attached to the larger laparoscopic tube. FIG. 7B illustrates a side view of the removable suture head. FIG. 7C illustrates a top-down view of the removable suture head. FIG. 7D illustrates an angled view of the removable suture head. FIGS. 8A-8C illustrate further CAD renderings of the automatic suturer in accordance with one or more embodiments of the invention. Specifically, FIGS. 8A-8C illustrate an open device 800 with visible forceps 802 that when closed will clamp onto the stomach issue securing the device and tissue in place. Slots (an upper and lower slot) 804 enable the insertion of the blade to cut the stomach issue as the blade moves through the lots 804. Tracks (upper and lower) 806 enable the movement of two needles 808 (one in each track) to suture the tissue before the blade cuts the tissue, simultaneously with the cutting of the tissue, or after the tissue has been cut.

Figure 9A:
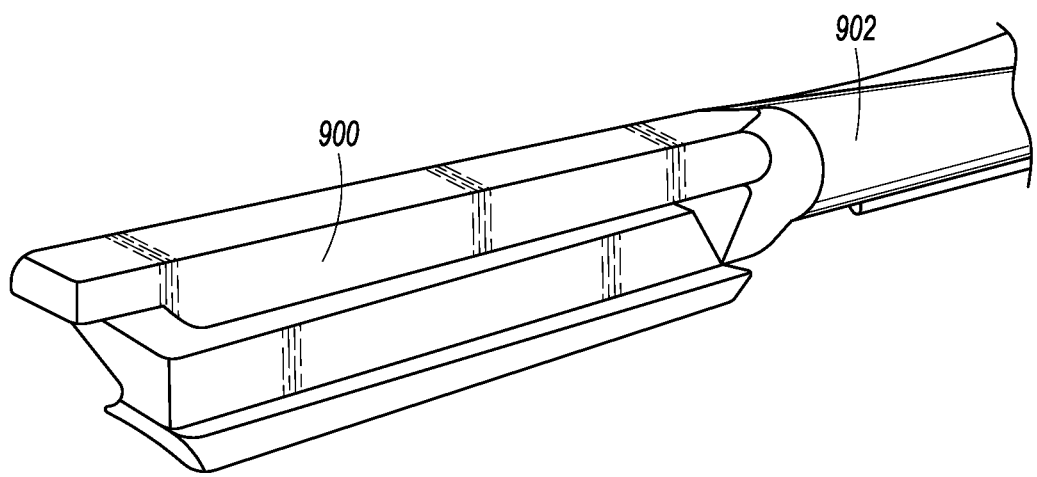
FIG. 9A illustrates a picture of a 3D printed model made of polylactic acid (PLA) of the CAD renderings of FIGS. 6A-6B in accordance with one or more embodiments of the invention.
Figure 9B:
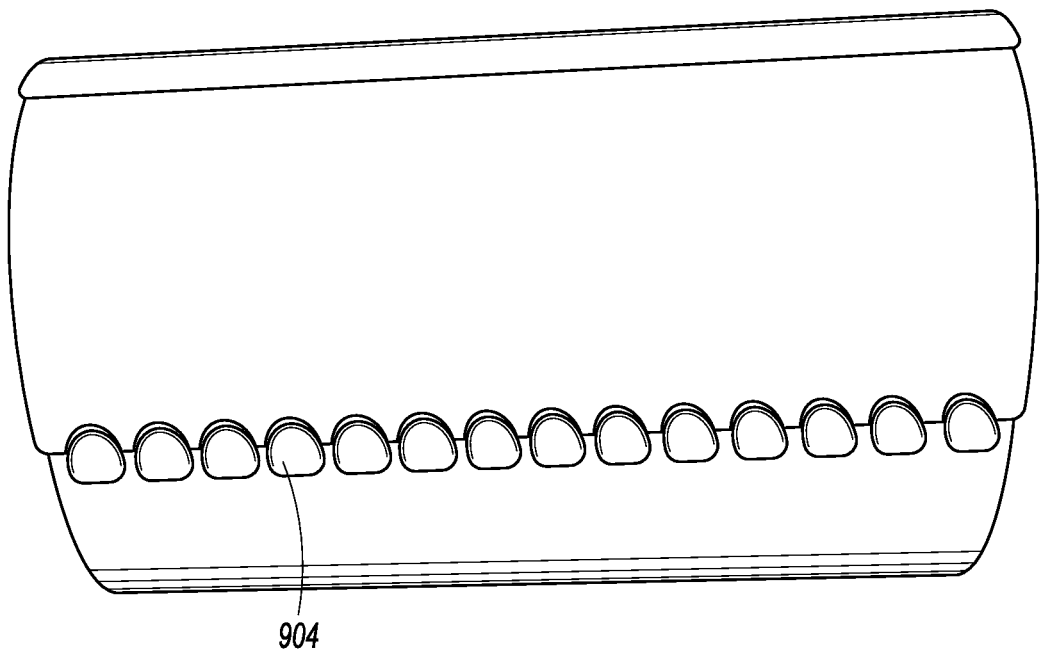
FIGS. 9B-9D illustrate pictures of a 3D printed model made of polylactic acid (PLA) of the CAD renderings of FIGS. 8A-8C in accordance with one or more embodiments of the invention.
Figure 9C:
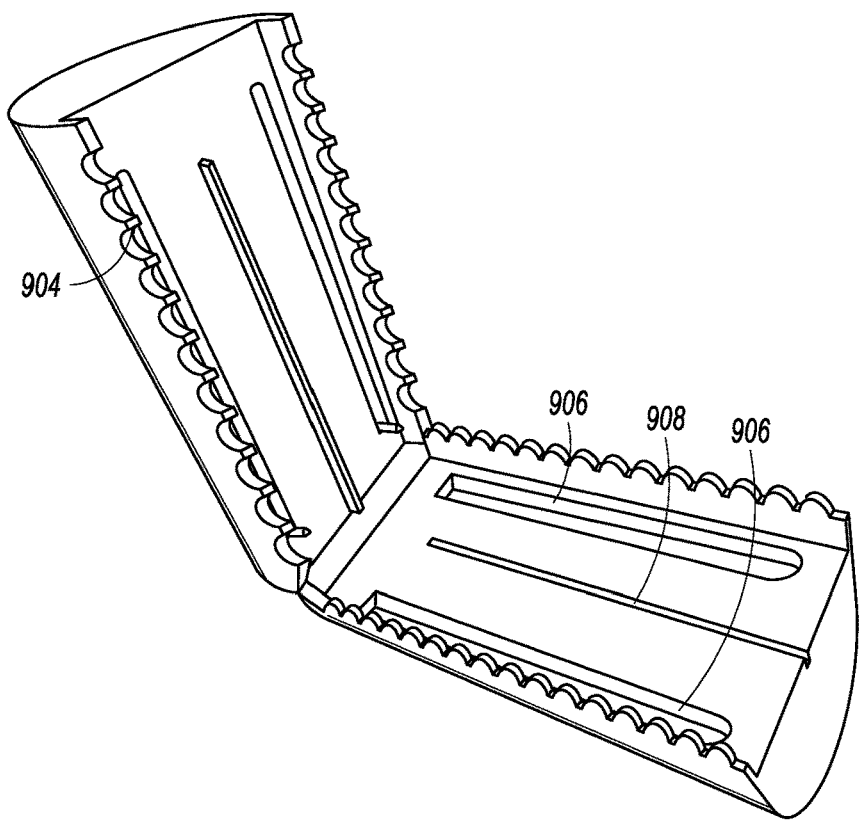
Figure 9D:
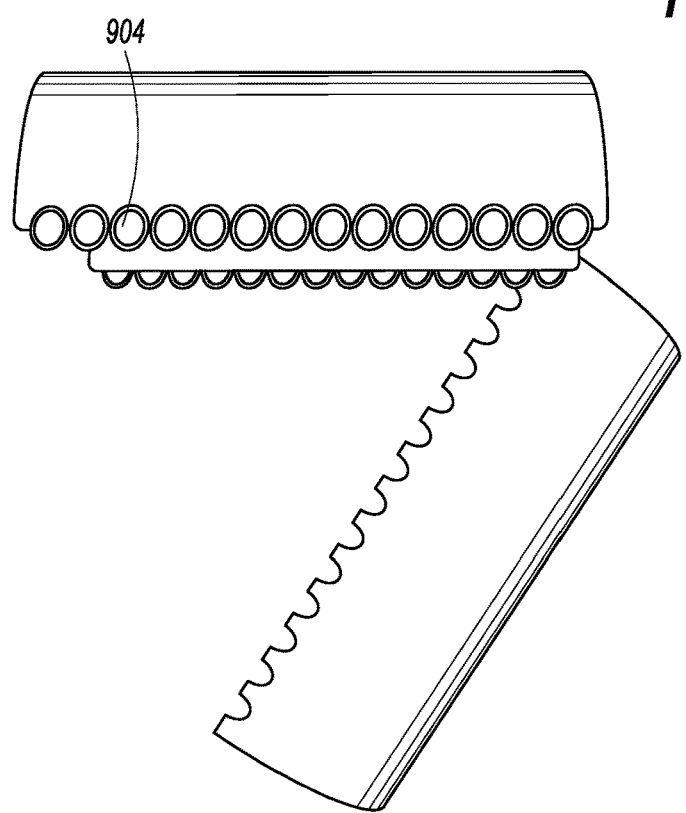

FIG. 9A illustrates a picture of a 3D printed model 902 made of polylactic acid (PLA) of the CAD renderings of FIGS. 6A-6B in accordance with one or more embodiments of the invention. Specifically, FIG. 9A illustrates a zoomed-in view of a closed prototype 900 with a laparoscopic arm 902. The model is designed to illustrate the actual appearance of the suture (e.g., its size and scale). As illustrated, the device may function laparoscopically and is in its closed or clamped position. FIGS. 9B-9D illustrate pictures of a 3D printed model 903 made of polylactic acid (PLA) of the CAD renderings of FIGS. 8A-8C in accordance with one or more embodiments of the invention. FIGS. 9B, 9C, and 9D illustrate a suture device in the closed (FIG. 9B) and open (FIGS. 9C and 9D) positions to illustrate the forcep teeth 904 (i.e., used to compress/clamp/grasp the tissue without causing any harm) and the two-track approach (i.e., needle tracks 906 and blade track 908), and may be utilized with straight and/or curved needles. In this regard, FIG. 9B illustrates a closed suturer device while FIGS. 9C and 9D illustrate the suture device open.

Figure 10A:
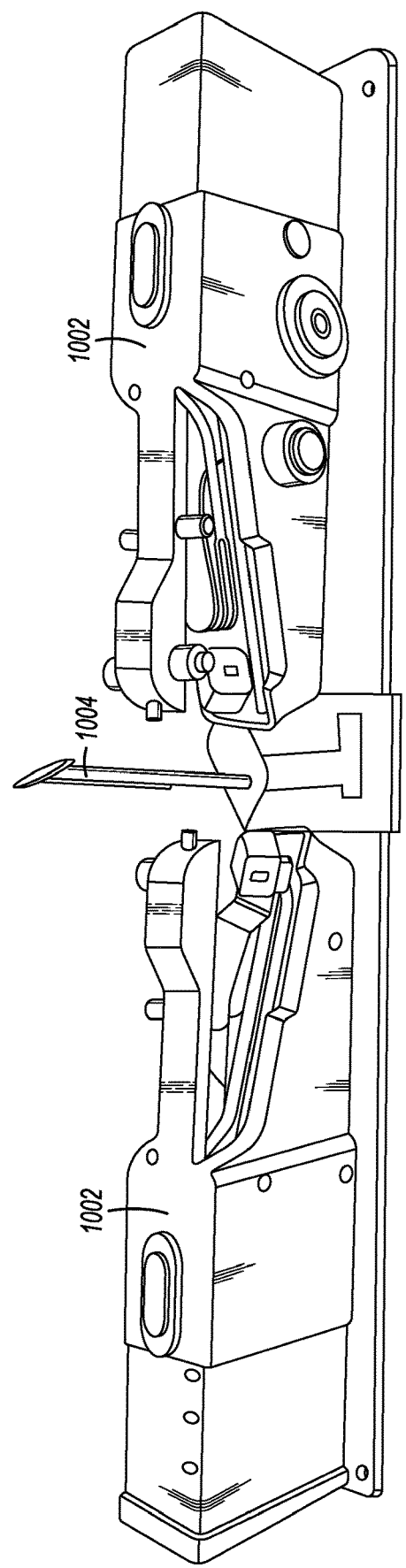
FIGS. 10A and 10B illustrate pictures of the mechanical functionality of a prototype automatic suturer in accordance with one or more embodiments of the invention.
Figure 10B:
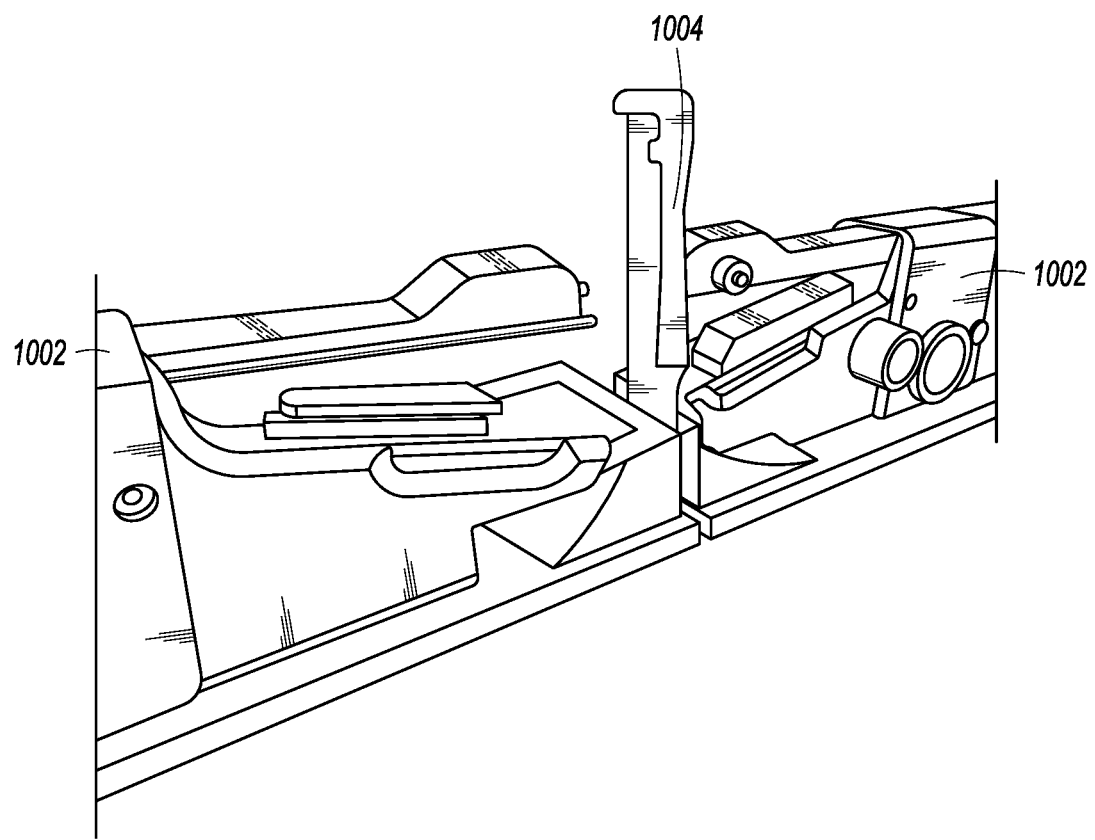

FIGS. 10A and 10B illustrate pictures of the mechanical functionality of a prototype automatic suturer in accordance with one or more embodiments of the invention. As illustrated, two automatic handheld sewing machines 1002 represent the two automatic suturing needles. These machines 1002 are positioned facing each other with a blade 1004 in the middle, with all the needles and blade 1004 able to be activated at the same time to enable simultaneous cutting and suturing on each side of an incision (i.e., the tissue to be cut would be located beneath blade 104 while the suturing devices 1002 would automatically suture the tissue dynamically as the tissue is incised. Referring to FIG. 10A, the device would be moved in a vertical direction to incise and suture simultaneously.

Figure 11:
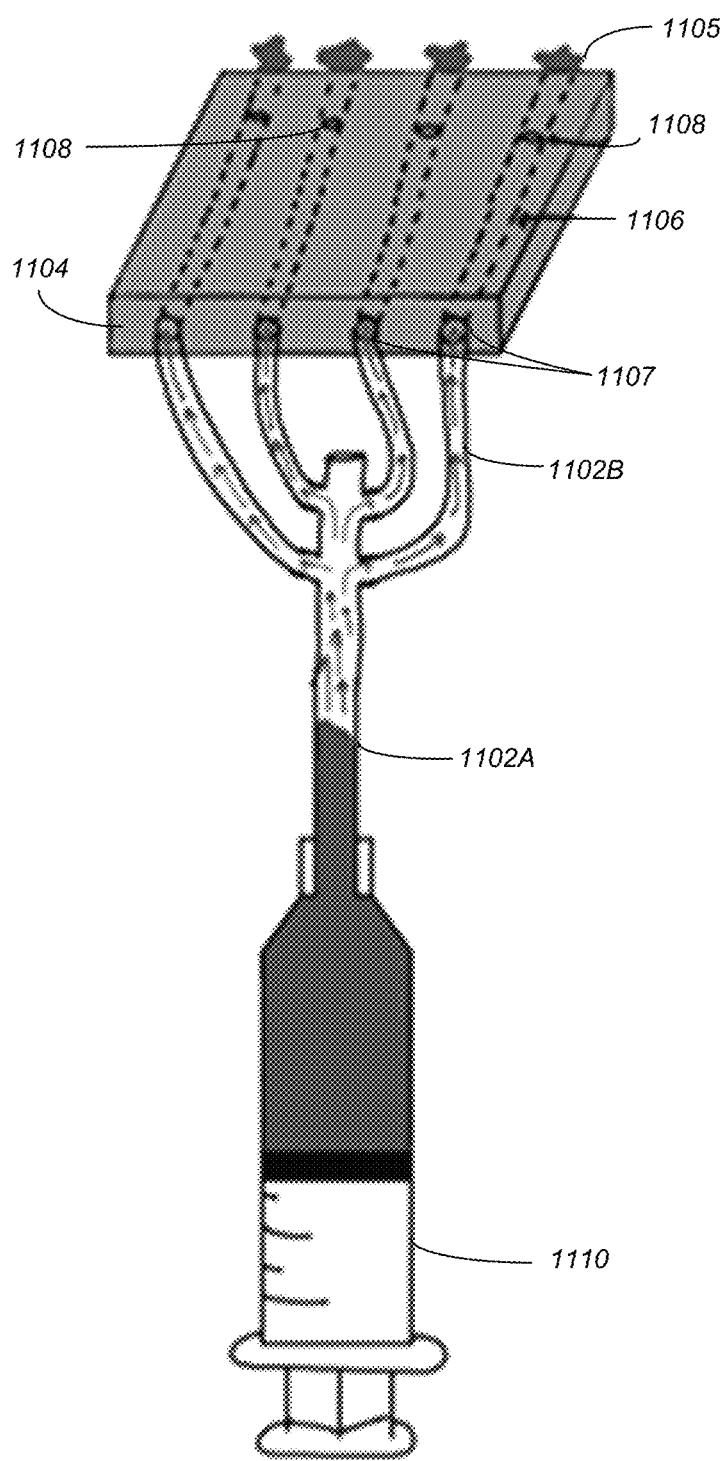
FIG. 11 illustrates a schematic of a model system to simulate bleeding in accordance with one or more embodiments of the invention.

To test the efficacy of the automatic suturer, the volume of blood lost along the incision is a metric that may be monitored. FIG. 11 illustrates a schematic of a model system to simulate bleeding in accordance with one or more embodiments of the invention. During testing, porcine stomach tissue was chosen to represent human stomach tissue, as the porcine stomach's structural properties are very similar to human tissue (so similar, in fact, that porcine stomach tissue is actually used to train surgical residents to perform gastric bypass surgery using the stapler). To simulate bleeding, a system of tubing was designed to mimic blood vessels. Plastic tubing 1102 (including main tube 1102A and smaller tubing 1102B that branches from the main tubing 1102A) with a diameter of 2 mm was inserted into the porcine tissue 1104, and pushed all the way through to the opposite end 1105 to mimic cutting the tissue 1104 (i.e., bleeding occurs at the end/edge 1105 of the skin 1104). In this regard, the tissue 1104 illustrated in FIG. 11 is a cross section so that the various other elements may be observed. After creating cylindrical cuts/holes 1106 (i.e., with an entrance at 1107 and exit at 1105 of tissue 1104) in the tissue surface (to allow for blood flow), the tubes 1102 were pulled back slightly to leave room for stapling/suturing (the pulled back location of the tubes is illustrated at 1108). The tubes 1102 were connected to a syringe 1110 filled with a mixture containing a 1:15 ratio of maple syrup to water in order to mimic the viscosity of blood ([Chen]).

Tissue 1104 bleeding was tested using this system under three different conditions. In each condition, 125 ml of mock blood was poured into the syringe 1110. The syringe 1110, tubes 1102, and tissue 1104 were held vertically, allowing gravity to force the blood downwards. This position was held for one minute, during which any bleeding was evacuated and collected in a receptacle underneath the tissue. After one minute, the receptacle was removed and the volume of mock blood was recorded.

The first condition tested was a negative control in which no sealing methods were used. As expected, bleeding occurred very rapidly (e.g., was evacuated rapidly from exit 1105), and all 125 ml were lost within 20 seconds. The second condition tested used stapling as a sealing method. In this condition, a standard Endo GIA stapler was used to seal the tissue 1104. Although data exists on blood volume lost through staple-lines, testing the Endo GIA stapler in the testing apparatus described herein was used to standardize results and ensure the test validity. The stapler was able to effectively seal much of the tissue, but did result in 10 ml of bleeding over the course of the minute. The third and final condition tested used suturing (i.e., embodiments of the invention) as a sealing method. In this condition, the tissue 1104 was sutured by hand, mimicking the pattern of the automatic suture design as closely as possible. Suturing was highly effective at sealing the tissue, and only 7 ml of blood were lost. The conditions and results of the testing are summarized in Table 8.

TABLE 8

| Condition | Volume of blood measured after one minute of bleeding | Rate of Blood Loss |
| --- | --- | --- |
| Control (no sealing) | 125 ml (maximum; all lost within 20 sec) | 6.25 ml/sec |
| Stapling | 10 ml | 0.17 ml/sec |
| Suturing | 7 ml | 0.12 ml/sec |

The test results indicate that suturing is more effective than stapling at sealing tissue 1104, and support the use of an automatic suturing device over a stapler. The calculations described above can be repeated to match the length of tissue cut/sealed during testing; using 60 mm instead of 280 mm in the final calculation yields a blood loss rate of 0.25 ml/sec. This rate is very similar to the rate observed in the stapling test condition, validating the testing model as an accurate reflection of the system. A bleeding rate of 0.25 ml/sec (15 ml/min) means it would take almost an hour for bleeding to reach a class II hemorrhage, providing sufficient time for the tissue to heal naturally or for the surgeon to use additional sealing methods if necessary.

Figure 12:
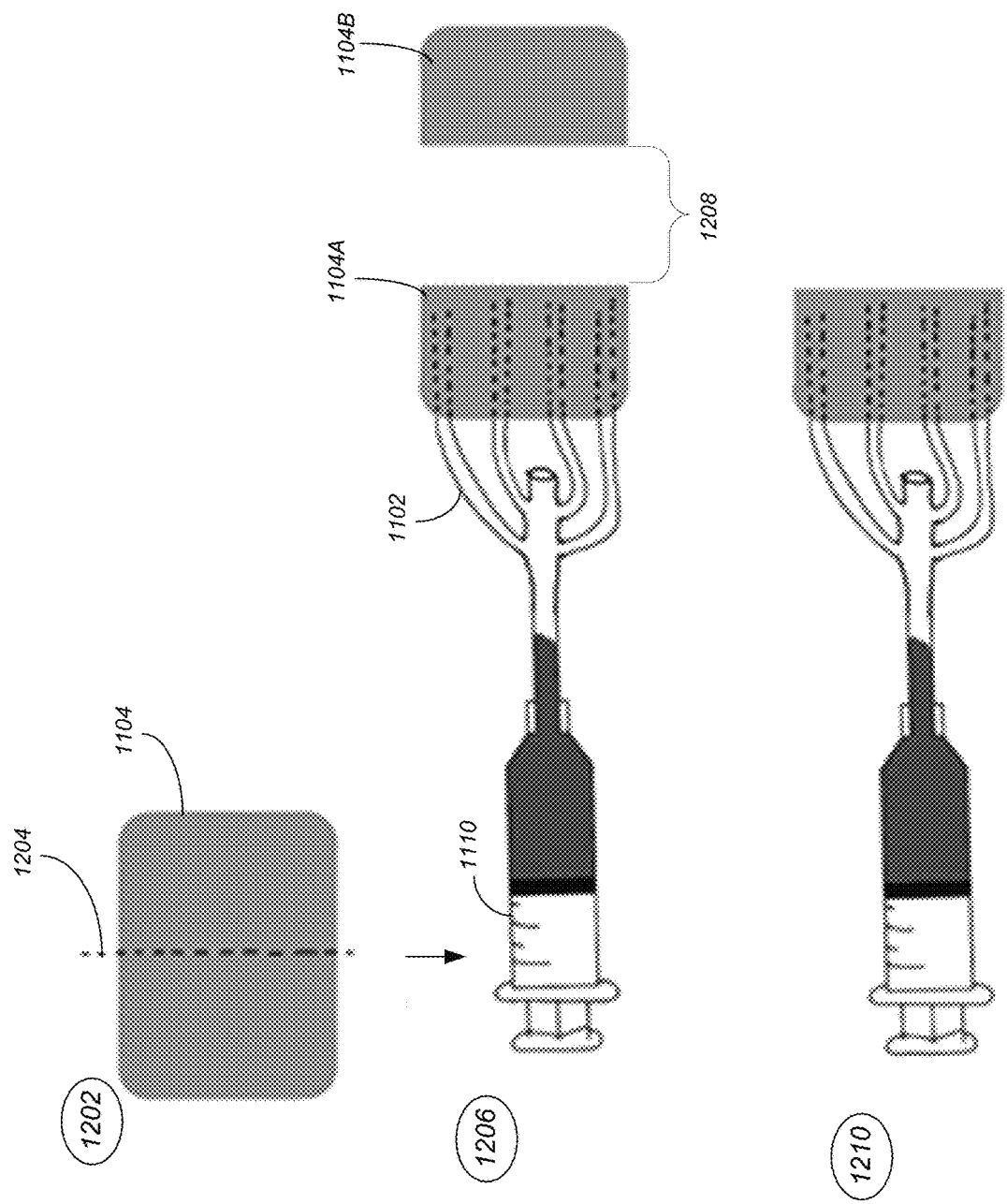
FIG. 12 describes the process for testing in accordance with one or more embodiments of the invention.

As described herein, the model tests the efficacy of staples versus sutures at preventing bleeding. More specifically, the model captures one half of the affected tissue. FIG. 12 describes the process for testing in accordance with one or more embodiments of the invention. At step 1202, the tissue 1104 is cut (i.e., along dotted line 1204). At step 1206, the tubing 1102 is inserted into tissue 1104 and connected to syringe 1110. Further, the tubing is inserted into the tissue 1104A opposite the side of the cut 1208 and pulled back slightly (i.e., indicated by the dotted lines not extending to the edge of tissue 1104). The second half of the tissue 1104 (i.e., tissue 1104B) may be discarded/thrown away for the testing. At step 1210, the testing (i.e., collection and measurement of mock blood) is conducted with the half of tissue 1104 that remains.

Alternative Embodiments

Figure 13:
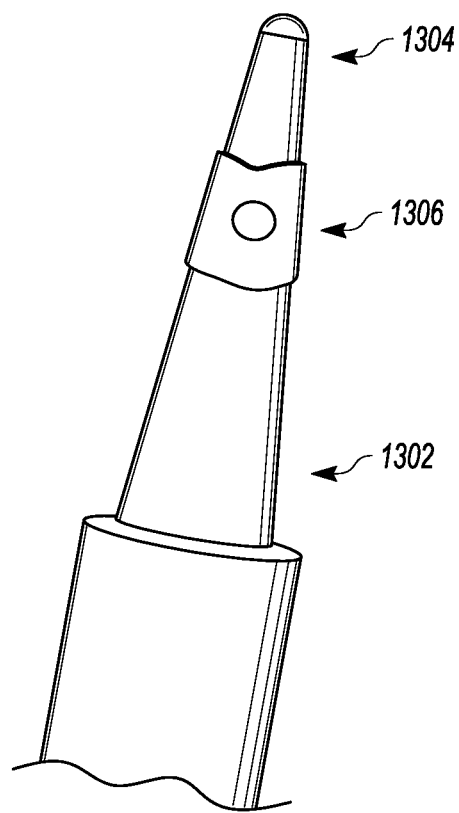
FIG. 13 illustrates a low-fidelity cauterizing needle in accordance with one or more embodiments of the invention.

Embodiments of the invention are not limited to the above-described implementations. For example, in one or more embodiments, an electronic system (e.g., a circuit/hardware that may be combined with software) could be used to control the device, Further to the above, embodiments of the invention may utilize needles in the suturer that are configured with ability to cauterize. Additionally, the suturer may integrate cautery through the use of an electrified needle. Such heated/self-cauterizing needles would cauterize the tissue as the needles move/progress through the tissue to form sutures, thereby further minimizing bleeding. In such embodiments, the needle itself may be heated, and the head of the needle may contain an insulated hole through which thread could be inserted without being burned/negatively affected by the direct/indirect heat from the needle head. FIG. 13 illustrates a low-fidelity cauterizing needle in accordance with one or more embodiments of the invention. As illustrated, the needle 1302 includes an insulated hole 1304 for thread and a cauterizing tip 1306.

Figure 14:
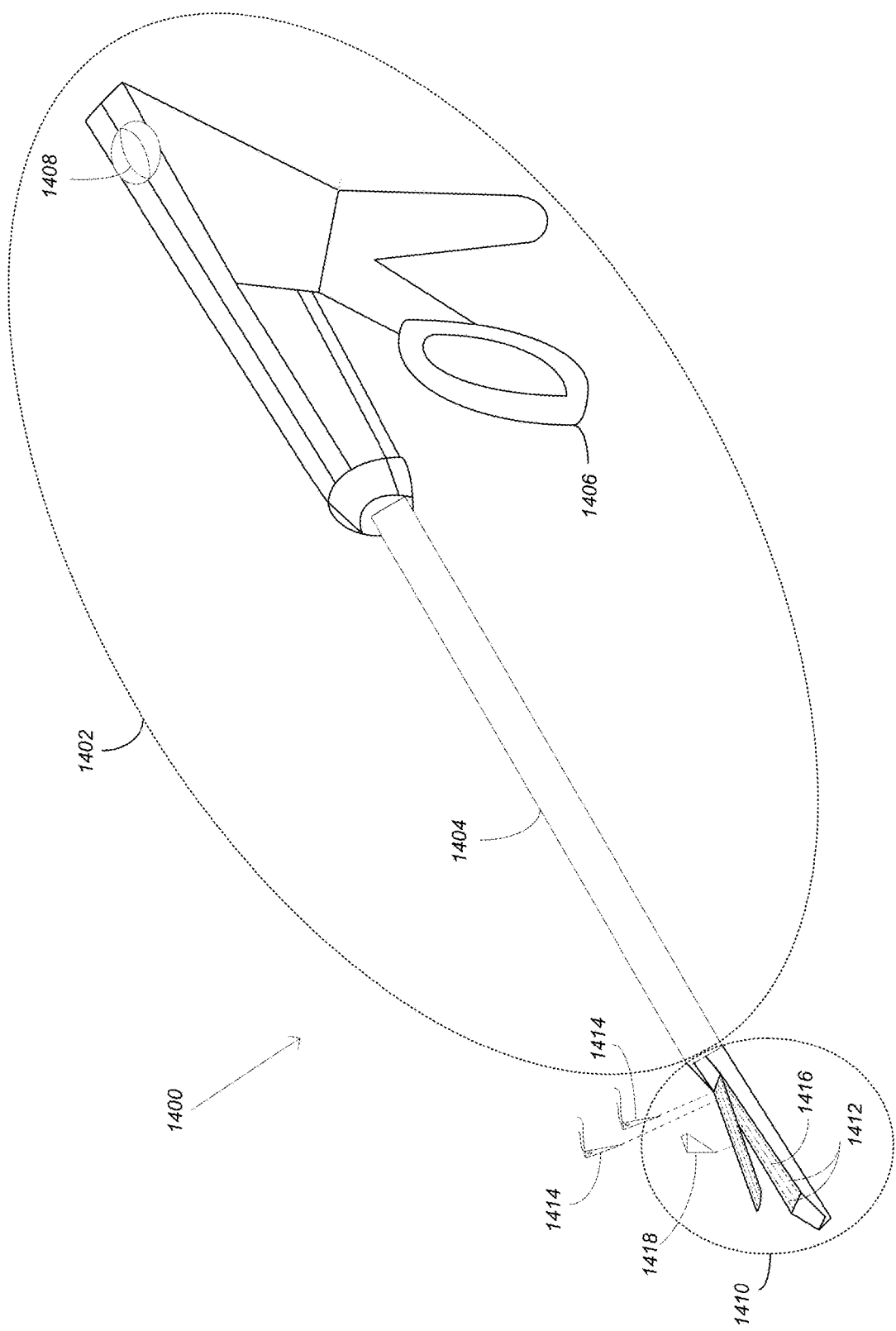
FIG. 14 illustrates an automatic suturing device that may be utilized in accordance with one or more embodiments of the invention.

FIG. 14 illustrates an automatic suturing device 1400 that may be utilized in accordance with one or more embodiments of the invention. The actuating device 1402 includes a laparoscopic extender 1404 for insertion into the patient. The extender 1404 is affixed/connected to the handle/trigger 1406 and an actuating button 1408 is used to control the suturing. The actuating device 1402 may be connected to a disposable reloadable suturing unit 1410. The disposable reloadable suturing unit 1410 is illustrated in the open position and includes tracks 1412 which the suturing needles 1414 travel along during the suturing, and track 1416 which the blade 1418 travels along to perform the tissue incision. The handle 1406 is used to close the disposable reloadable suturing unit 1410 and locked the unit 1410 in place. Once secured in the closed position, the actuating button 1408 may be depressed to actuate the unit 1410 thereby causing the blade 1418 to traverse through track 1416 incising the tissue while simultaneously causing the needles 1414 to travel/bob through tracks 1412 to suture the tissue. While only two needles 1414 are illustrated, embodiments of the invention may utilize additional needles (e.g., one for each stitch, or adjacent needles to enable an overlapping suture pattern) and/or the disposable unit 1410 may also include a capability to both staple and suture simultaneously. Once the stitching is complete, the cauterizing capability of the needle may seal the tissue and/or enable the thread to form a seal on the tissue surface (e.g., a knot may be formed and/or the end of the thread may be melted thereby forming an enlarged area such that the thread cannot slip back through the hole formed by the needle). For example, the suture may be manually terminated by a surgeon. Alternative embodiments for terminating the suturing as known in the surgical field may be used in either an automated or manual manner. Further, as described above, the actuating button 1408 may consist of an electronic actuator connected to an IDE to control the cutting/suturing.

Logical Flow

Figure 15:
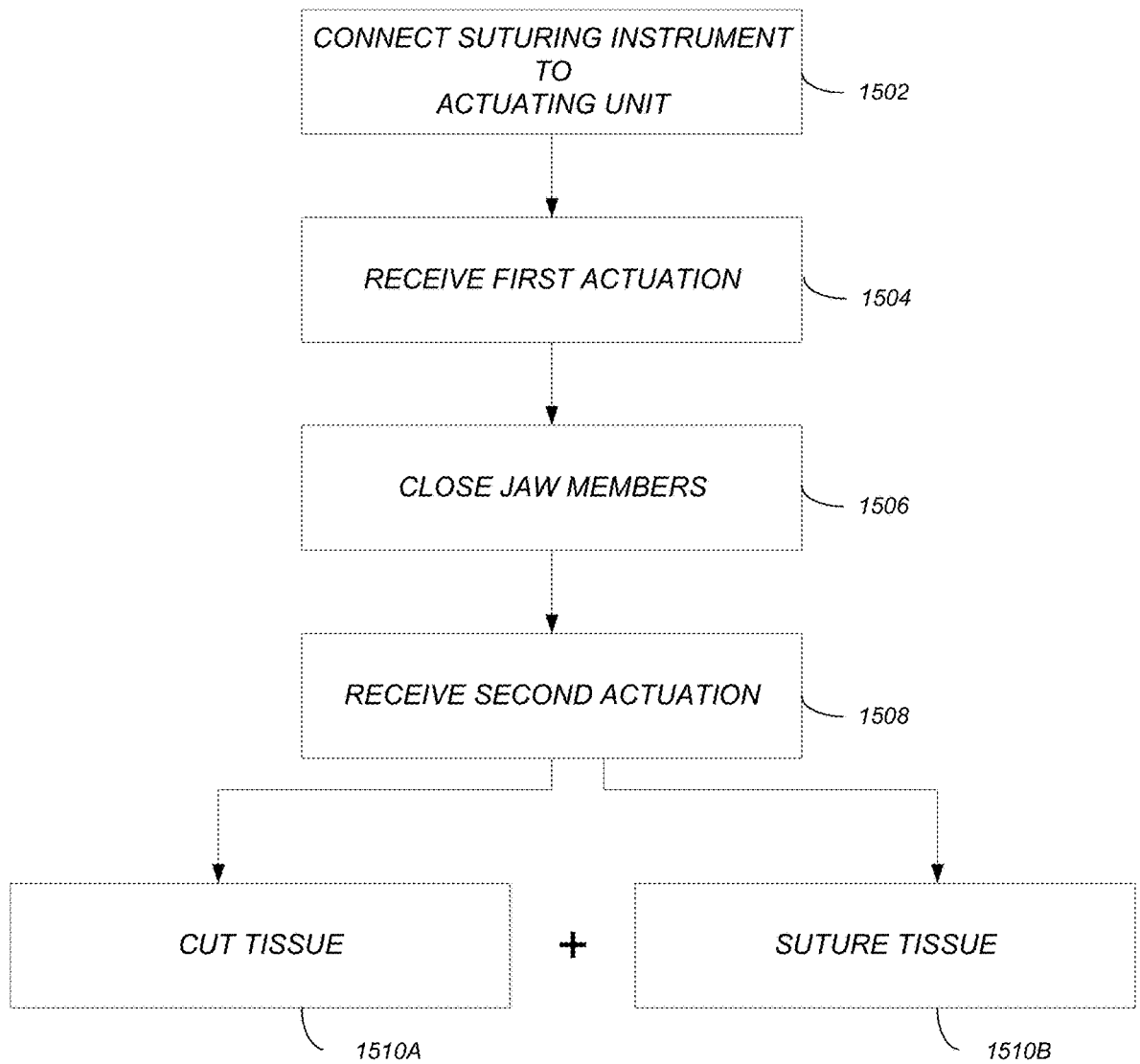
FIG. 15 illustrates the logical flow for suturing tissue in accordance with one or more embodiments of the invention.

FIG. 15 illustrates the logical flow for suturing tissue in accordance with one or more embodiments of the invention.

At step 1502, a disposable reloadable laparoscopic suturing instrument is connected to an actuating unit. The disposable reloadable laparoscopic suturing instrument includes a pair of first and second opposable jaw members, a blade unit, and two or more needle units.

At step 1504, a first actuation (of the pair of first and second opposable jaw members) is received (in the disposable reloadable laparoscopic suturing instrument) from the actuating unit. The pair of jaw members includes a blade track and a pair of two or more needle tracks. Further, the blade track is located between at least two of the two or more needle tracks. In addition, the pair of jaw members may include forcep teeth that grasp the tissue without causing any harm to the tissue. In addition, the needle tracks (and blade track) are all likely parallel to each other. To control the actuating, the actuating instrument may include a handle that is depressed.

At step 1506, in response to the first actuation, the pair of jaw members is closed. Once closed, the pair of jaw members clamp onto and secure the tissue upon which the pair of jaw members have been placed.

At step 1508, a second actuation actuating the blade unit and the two or more needle units is received in the disposable reloadable laparoscopic suturing instrument. The second actuation may be an electronic actuation. Such a second actuation may include actuation via a circuit/hardware and/or software, blue tooth, or other communication means.

At step 1510, in response to receiving the second actuation, two actions are performed. In step 1510A, a blade in the blade unit travels along the blade track, of the jaw members, cutting the tissue that has been secured by the pair of jaw members resulting in an incision. In step 1510B, a needle and thread in each of the needle units travel along a respective needle track, of the two or more needle tracks of the jaw members, suturing the tissue secured by the pair of jaw members. In one or more embodiments, each needle/needle unit may move laterally within the respective needle track to thread a precisely defined line. Once sutured, the tissue is sealed on both sides of the incision. Such a sealing results in less blood leakage (from the tissue) (i.e., a lower blood leakage rate) compared to that of prior art devices that utilize staples. In one or more embodiments, the cutting and suturing (i.e., steps 1510A and 1510B) are conducted simultaneously with each other as both the blade and pair of needles move along the blade track and pair of needle tracks.

Further to the above, the needles may be curved suturing needles and may also be self-cauterizing needles.

CONCLUSION

This concludes the description of the preferred embodiment of the invention. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[Silecchia] Silecchia G. Complications of staple line and anastomoses following laparoscopic bariatric surgery. Annals of Gastroenterology. 2017 Oct. 12.

[Gundogan] Gundogan E, Kayaalp C, Aktas A, Saglam K, Sansal M, Uylas U, et al. Randomized controlled trial of monopolar cautery versus clips for staple line bleeding control in Roux-en-Y gastric bypass. International Journal of Surgery. 2018 May 16; 58:52-6.

[Gastric] Gastric Bypass Surgery [Internet]. Gastric Bypass Surgery|Columbia University Department of Surgery. [cited 2019 Dec. 10]. Available from: https://columbia-surgery.com/conditionis-and-treatments/gastric-bypass-surgery

[Kasemo] Kasemo B. Biocompatibility of titanium implants: Surface science aspects. The Journal of Prosthetic Dentistry. 1983 June; 49(6):832-7.

[Sánchez-Margallo] Sanchez-Margallo F M, Sánchez-Margallo J A, Amir, Szold. Handheld Devices for Laparoscopic Surgery [Internet]. IntechOpen. IntechOpen; 2018 [cited 2019 Dec10]. Available from: https://www.intechopen.com/book/new-horizons-in-laparoscopic-surgery/handheld-devices-for-laparoscopic-surgery

[Nilsson] Nilsson B, Ekdahl K N, Mollnes T E, Lambris J D. The role of complement in biomaterial-induced inflammation. Molecular Immunology. 2007 January; 44(1-3): 82-94.

[Jacobsen] Jacobsen H J, Nergard B J, Leifsson B G, Frederiksen S G, Agajahni E, Ekelund M, et al. Management of suspected anastomotic leak after bariatric laparoscopic Roux-en-y gastric bypass. British Journal of Surgery. 2014; 101(4):417-23.

[Lipscomb] Lipscomb V. Surgical staplers. BSAVA Companion. 2012 January; 2012(1):12-3.

[Webmaster] Webmaster SAGES. MicroCutter XCHANGE 30 Stapler: 5 mm articulating minimally-invasive stapler.—A SAGES Technology and Value Assessment [Internet]. SAGES. [cited 2019 Dec. 10]. Available from: https://www.sages.org/publications/tavic/microcutter-xchange-30-stapler-5mm-articulating-minimally-invasive-stapler/

[Schirmer] Schirmer B D. 27 Laparoscopic Gastric Bypass Using Linear Stapling Technique. Minimally Invasive Bariatric Surgery. 2014; 249-54.

[Canonico] Canonico S. The use of human fibrin glue in the surgical operations [Internet]. Acta bio-medica: Atenei Parmensis. U.S. National Library of Medicine; 2003 [cited 2019 Dec. 10]. Available from: https://www.ncbi.nlm.nib.gov/pubmed/15055028

[Bryans] Bryans T. Poster Highlights Sterility Assurance Levels. Biomedical Instrumentation & Technology. 2010; 44(3):240-1.

[Endo] Endo GIA™ Universal Staplers Product Support [Internet]. Medtronic. [cited 2019 Dec. 10]. Available from: https://www.medtronic.com/covidien/en-us/support/products/surgical-stapling/endo-gia-universal-staplers-and-reloads.html

[He] He H, Zhang L, Guan X, Cheng H, Liu X, Yu S, et al. Biocompatible Conductive Polymers with High Conductivity and High Stretchability. ACS Applied Materials & Interfaces. 2019; 11(29):26185-93.

U.S. Pat. No. 7,828,798B2—Laparoscopic bipolar electrosurgical instrument.

US20050021026A1—Method of fusing biomaterials with radiofrequency energy.

U.S. Pat. No. 8,303,585B2—Combined dissecting, cauterizing, and stapling device

US20160228145A1—Surgical stapling instrument having ultrasonic energy delivery

[Kvietys] Kvietys P R. The Gastrointestinal Circulation. San Rafael (CA): Morgan & Claypool Life Sciences; 2010. Chapter 2, Anatomy. Available from: https://www.ncbi.nlm/nih.gov/books/NBK53099/

[Paxton] Paxton, Steve, Peckham, Michelle, Knibbs, Adele. The Leeds Histology Guide [Internet]. The Histology Guide. University of Leeds; 1970 [cited 2019 Dec. 11]. Available from: https://www.histology.leeds.ac.uk/circulatory/arteries.php

[Blood Flow] Blood Flow, Blood Pressure, and Resistance [Internet]. Anatomy and Physiology. OpenStax; 2013 [cited 2019 Dec. 10]. Available from: pressure; https://opentextbc.ca/anatomyandphysiology/chapter/20-2-blood-flow-blood-pressure-and-resistance/

[Manning] Manning J E (2003-11-04). "Fluid and Blood Resuscitation". In Tintinalli J E, Kelen G D, Stapczynski J S (eds.). *Emergency Medicine: A Comprehensive Study Guide, Sixth edition*. McGraw Hill Professional. p. 227. ISBN 978-0-07-150091-3.

[Woodford] Woodford C. How do sewing machines work? [Internet]. Explain that Stuff. 2019 [cited 2019 Dec. 10]. Available from: https://www.explainthatstuff.com/sewingmachines.html

[Chen] Chen H, Li J, Perkins T. Rheological and Colorimetry Properties of Maple Syrup. 2001 Sacramento, Calif. Jul. 29-Aug. 1, 2001;

What is claimed is:

1. A laparoscopic suturing instrument comprising:
    (a) the laparoscopic suturing instrument configured to connect to and receive control signals via an actuating instrument;
    (b) a pair of first and second opposable jaw members, wherein:
        (i) upon the actuating instrument controlling the pair of jaw members to close, the pair of jaw members clamp onto and secure the tissue upon which the pair of jaw member have been placed;
        (ii) the pair of jaw members comprise a blade track and a pair of two or more needle tracks; and
        (iii) the blade track is located between at least two of the two or more needle tracks;
    (c) a blade unit comprising a blade that, upon actuation from the actuating instrument, travels along the blade track cutting the tissue that has been secured by the pair of jaw members resulting in an incision; and
    (d) two or more needle units, with each needle unit comprising a needle and thread that, upon actuation from the actuating instrument, travels along a respective one of the needle tracks suturing the tissue secured by the pair of jaw members, wherein once sutured, the tissue is sealed on both sides of the incision, and wherein at least one of the two or more needle units comprises multiple adjacent needles that suture in an overlapping suture pattern.

2. The laparoscopic suturing instrument of claim 1, wherein the pair of jaw members comprise forcep teeth that grasp the tissue without causing any harm to the tissue.

3. The laparoscopic suturing instrument of claim 1, wherein:
    the cutting and suturing are conducted simultaneously with each other as both the blade and pair of needles move along the blade track and pair of needle tracks.

4. The laparoscopic suturing instrument of claim 1, wherein:
    the needles comprise self-cauterizing needles, wherein at least one of the self cauterizing needles seals the tissue and melts the thread thereby forming an enlarged area such that the thread cannot slip back through a hole formed by the at least one self cauterizing needle.

5. The laparoscopic suturing instrument of claim 1, wherein:
    the actuating instrument controls the pair of jaw members to close via a handle that is depressed.

6. The laparoscopic suturing instrument of claim 1, wherein:
    the actuation actuating the cutting and suturing are electronically actuated.

7. The laparoscopic suturing instrument of claim 1, wherein:
    each of the needle units further comprises a stapler;
    the stapler staples the tissue simultaneously with the suturing.

8. The laparoscopic suturing instrument of claim 7, wherein:
    the stapler staples the tissue using a triangle staple pattern.

9. The laparoscopic suturing instrument of claim 7, wherein:
    one or more staples in the stapler comprise conductive biocompatible polymers; and
    the staples cauterize the tissue.

10. The laparoscopic suturing instrument of claim 7, wherein:
the stapler comprises an ultrasonic stapler; and
the stapler comprises a harmonic scalpel that cuts the tissue using frictional energy.

11. A method for suturing tissue comprising:
(a) connecting a laparoscopic suturing instrument to an actuating unit, wherein the laparoscopic suturing instrument comprises a pair of first and second opposable jaw members, a blade unit, and two or more needle units;
(b) receiving, in the laparoscopic suturing instrument, a first actuation, from the actuating unit, of the pair of first and second opposable jaw members, wherein:
  (i) the pair of jaw members comprise a blade track and a pair of two or more needle tracks; and
  (ii) the blade track is located between at least two of the two or more needle tracks;
(c) in response to the first actuation, closing the pair of jaw members, wherein once closed, the pair of jaw members clamp onto and secure the tissue upon which the pair of jaw members have been placed;
(d) receiving, in the laparoscopic suturing instrument, a second actuation, wherein the second actuation actuates the blade unit and the two or more needle units;
(e) in response to the second actuation, a blade in the blade unit travels along the blade track, of the jaw members, cutting the tissue that has been secured by the pair of jaw members resulting in an incision; and
(f) in response to the second actuation, a needle and thread in each of the needle units travel along a respective needle track, of the two or more needle tracks of the jaw members, suturing the tissue secured by the pair of jaw members, wherein once sutured, the tissue is sealed on both sides of the incision, and wherein at least one of the two or more needle units comprises multiple adjacent needles that suture in an overlapping suture pattern.

12. The method of claim 11, wherein the pair of jaw members comprise forcep teeth that grasp the tissue without causing any harm to the tissue.

13. The method of claim 11, wherein:
the cutting and suturing are conducted simultaneously with each other as both the blade and pair of needles move along the blade track and pair of needle tracks.

14. The method of claim 11, wherein:
the needles comprise self-cauterizing needles.

15. The method of claim 11, wherein:
the actuating instrument controls the first actuation via a handle that is depressed.

16. The method of claim 11, wherein:
the second actuation actuating the cutting and suturing are electronically actuated.

17. The method of claim 11, wherein:
each of the needle units further comprises a stapler;
the stapler staples the tissue simultaneously with the suturing.

18. The method of claim 17, wherein:
the stapler staples the tissue using a triangle staple pattern.

19. The method of claim 17, wherein:
one or more staples in the stapler comprise conductive biocompatible polymers; and
the staples cauterize the tissue.

20. The method of claim 17, wherein:
the stapler comprises an ultrasonic stapler; and
the stapler comprises a harmonic scalpel that cuts the tissue using frictional energy.

* * * * *